United States Patent
Awtrey et al.

(10) Patent No.: US 12,364,527 B2
(45) Date of Patent: Jul. 22, 2025

(54) APPARATUSES AND METHODS FOR CORRECTING BONE DEFORMITIES

(71) Applicant: Wright Medical Technology, Inc., Memphis, TN (US)

(72) Inventors: George Matthew Awtrey, Bartlett, TN (US); Robert Michael Carlo, Lakeland, TN (US); Zachary Korman, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 363 days.

(21) Appl. No.: 17/756,142

(22) PCT Filed: Jan. 25, 2021

(86) PCT No.: PCT/US2021/014841
§ 371 (c)(1),
(2) Date: May 18, 2022

(87) PCT Pub. No.: WO2021/154625
PCT Pub. Date: Aug. 5, 2021

(65) Prior Publication Data
US 2022/0395308 A1     Dec. 15, 2022

Related U.S. Application Data
(60) Provisional application No. 62/966,740, filed on Jan. 28, 2020.

(51) Int. Cl.
*A61B 17/66*     (2006.01)
*A61B 17/17*     (2006.01)
(Continued)

(52) U.S. Cl.
CPC ...... *A61B 17/8866* (2013.01); *A61B 17/1775* (2016.11); *A61B 17/66* (2013.01); *A61B 2017/565* (2013.01)

(58) Field of Classification Search
CPC ............ A61B 17/8866; A61B 17/1775; A61B 17/8872; A61B 17/885; A61B 2017/565
See application file for complete search history.

(56) References Cited

U.S. PATENT DOCUMENTS

| 6,409,729 B1 * | 6/2002 | Martinelli .......... A61B 17/6466 606/59 |
| 7,507,240 B2 * | 3/2009 | Olsen ................. A61B 17/6475 606/57 |

(Continued)

FOREIGN PATENT DOCUMENTS

WO     2020180598 A1     9/2020

OTHER PUBLICATIONS

International Search Report and Written Opinion for PCT/US2021/014841 issued Apr. 16, 2021, 16 pages.

(Continued)

*Primary Examiner* — Tracy L Kamikawa
(74) *Attorney, Agent, or Firm* — DUANE MORRIS LLP

(57) ABSTRACT

A device includes a first arm and a second arm. The first arm includes a first arm body that extends from a first end to a second end and a guide. The guide is rotatably coupled to the second end of the first arm body and is configured to be coupled to a first bone. The second arm includes a second arm body extending from a first end to a second end and is coupled to the first arm body such that it is rotatable with respect to the first arm body. The second arm is configured to engage a second bone. In use, rotation of the second arm body with respect to the first arm body changes the distance between the first bone and the second bone and rotation of (Continued)

the guide with respect to the first arm body rotates the first bone.

17 Claims, 31 Drawing Sheets

(51) Int. Cl.
*A61B 17/88* (2006.01)
*A61B 17/56* (2006.01)

(56) References Cited

U.S. PATENT DOCUMENTS

| | | |
|---|---|---|
| 9,301,782 B2 * | 4/2016 | Myers ................ A61B 17/6416 |
| 9,339,319 B2 * | 5/2016 | Schmuck ........... A61B 17/2804 |
| 9,622,805 B2 | 4/2017 | Santrock et al. |
| 2011/0098757 A1 | 4/2011 | Schelling |
| 2014/0031882 A1 | 1/2014 | Schmuck et al. |
| 2015/0313640 A1 | 11/2015 | O'Daly |
| 2016/0367291 A1 * | 12/2016 | Erickson ............ A61B 17/6416 |
| 2017/0113330 A1 * | 4/2017 | Williams .................. B25B 7/18 |
| 2017/0181757 A1 * | 6/2017 | Viola ..................... A61B 17/17 |
| 2018/0185079 A1 | 7/2018 | Smith et al. |
| 2019/0046235 A1 | 2/2019 | Waisman et al. |

OTHER PUBLICATIONS

Extended European Search Report issued in connection with corresponding European Patent Application No. 21748411.2, Sep. 29, 2023, 8 pages.

* cited by examiner

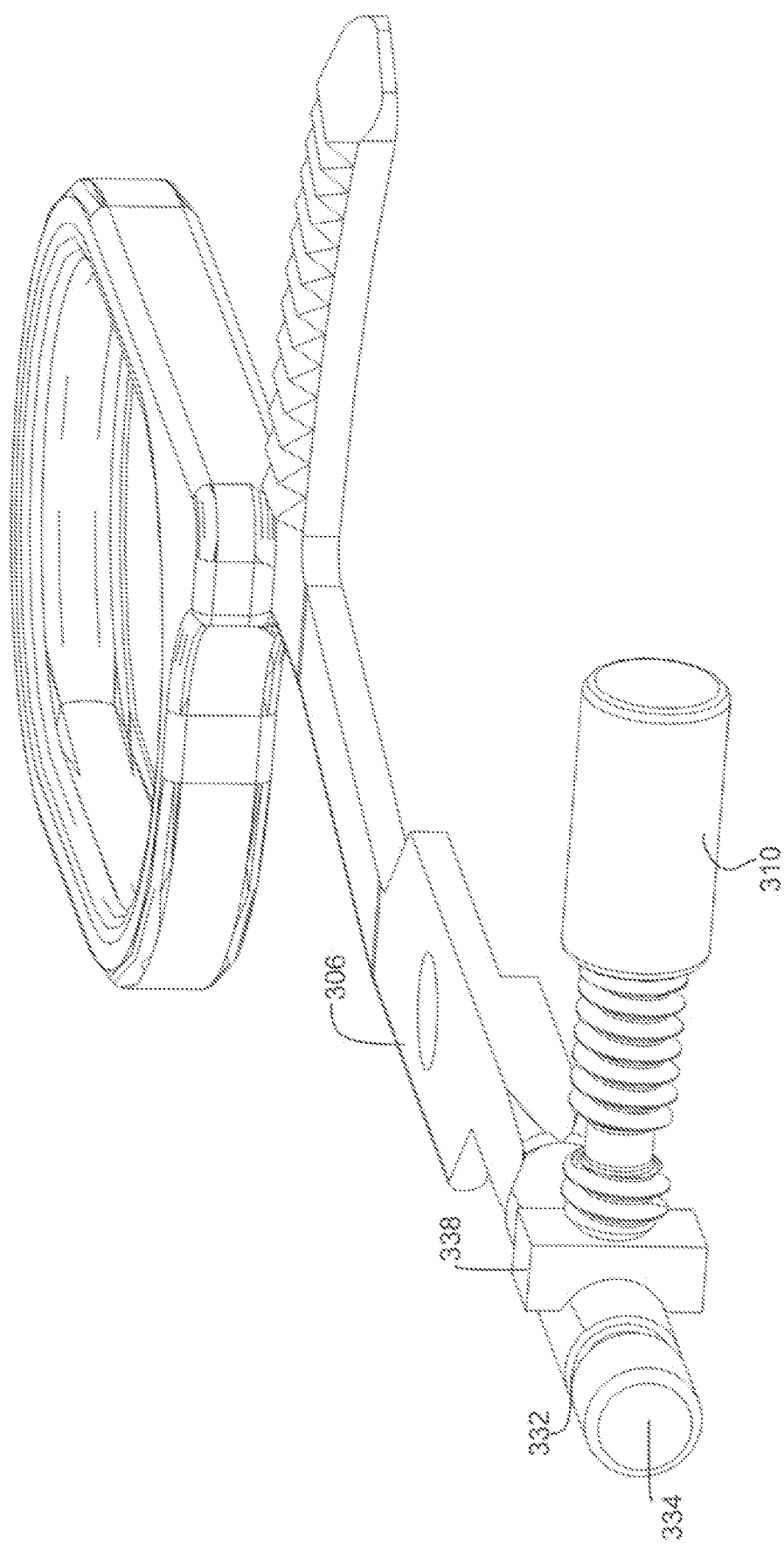

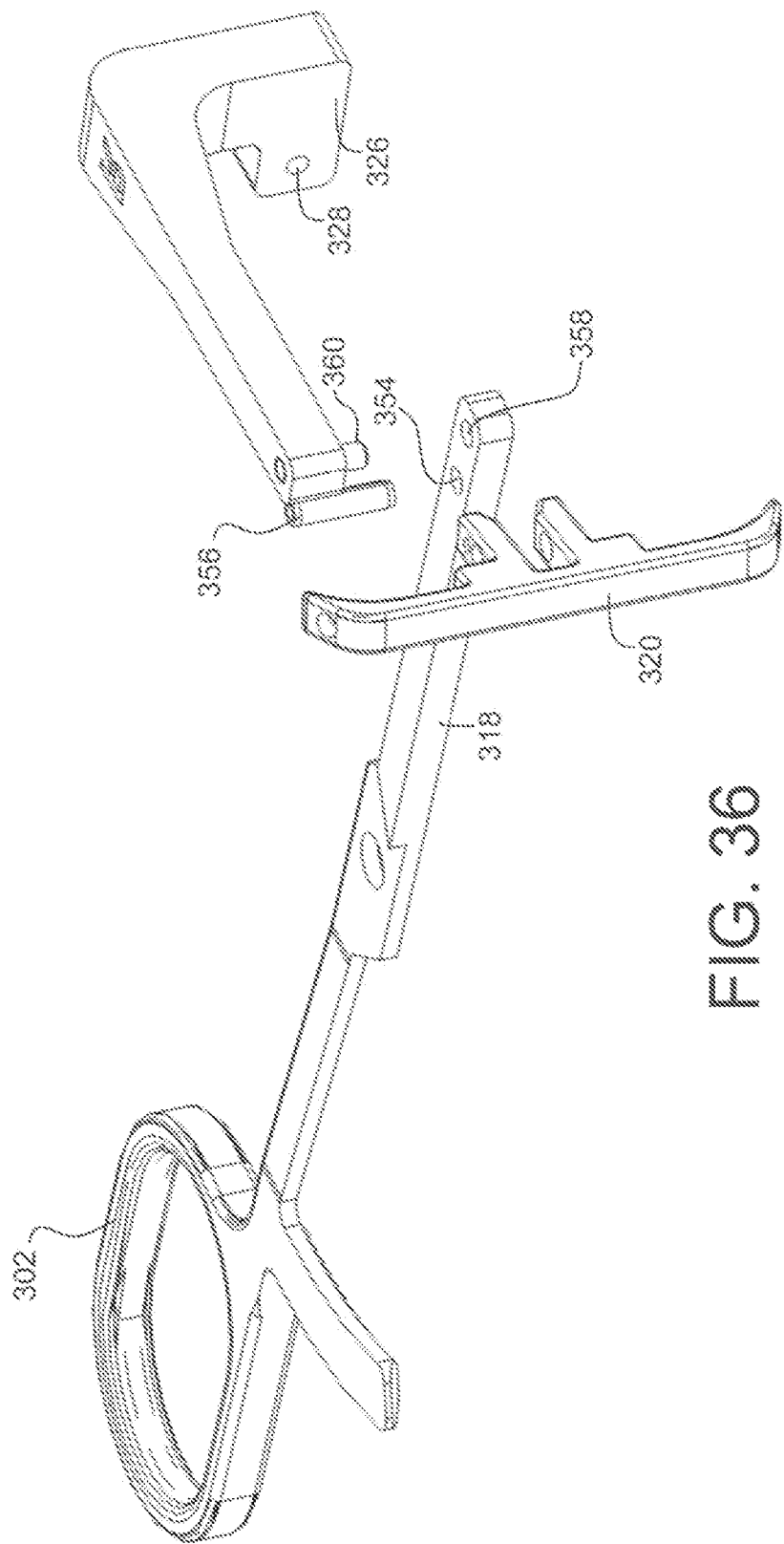

APPARATUSES AND METHODS FOR CORRECTING BONE DEFORMITIES

This application is a National Stage Application, filed under 35 U.S.C. 371, of International Patent Application No. PCT/US2021/014841, filed on Jan. 25, 2021, which claims priority to U.S. Provisional Patent Application No. 62/966,740, filed on Jan. 28, 2020, the entireties of which are incorporated herein by reference.

TECHNICAL FIELD

This disclosure relates generally to surgical tools, and more specifically to apparatuses and methods for correcting increased hallux valgus angle.

BACKGROUND

Hallux valgus deformities in the human foot relate to a condition in which the first (great) toe has a deviated position leaning in towards the second toe. The first metatarsal deviates towards the mid-sagittal plane, and the great toe deviates away from the mid-sagittal plane. This is often accompanied by a bump due to a swollen bursal sac or a bony anomaly on the metatarsophalangeal joint.

A variety of non-surgical methods are used to treat hallux valgus, but in cases of continued pain or visible deformity, the patient may seek a surgical correction of the condition. Surgical methods may include removing the bony enlargement of the first metatarsal, realigning the first metatarsal bone relative to the adjacent metatarsal bone, and/or straightening the great toe relative to the first metatarsal and adjacent toes.

One such method of treating hallux valgus deformities is known as a Lapidus procedure. In a Lapidus procedure, the first metatarsal is realigned and then the first tarsal-metatarsal joint is fused to decrease the movement of the joint. This straightens the first metatarsal and toe to reduce or eliminate the hallux valgus deformity.

SUMMARY

In one aspect, a device includes a first arm and a second arm. The first arm includes a first arm body and a guide. The first arm body extends from a first end to a second end. The guide is coupled to the second end of the first arm body. The guide is configured to be coupled to a first bone. The guide is rotatable with respect to the first arm body. The second arm includes a second arm body extending from a first end to a second end. The second arm body is coupled to the first arm body such that the second arm body is rotatable with respect to the first arm body about a rotation axis. The second arm is configured to engage a second bone at the second end of the second arm body. In use, rotation of the second arm body with respect to the first arm body changes the distance between the first bone and the second bone and rotation of the guide with respect to the first arm body rotates the first bone about a longitudinal axis of the first bone.

In another aspect, a device includes a first arm and a second arm. The first arm includes a first arm body, a guide, and a locking screw. The first arm body extends from a first end to a second end. The guide is coupled to the first arm body. The guide is coupleable to a first bone. The guide is rotatable with respect to the first arm body about a guide axis. The second arm includes a second arm body extending from a first end to a second end. The locking screw is coupled to the guide. Rotation of the locking screw in a first direction locks rotation of the guide and rotation of the locking screw in a second direction releases rotation of the guide. The second arm body is coupled to the first arm body such that the second arm body is rotatable with respect to the first arm body about a rotation axis. The second arm is configured to engage a second bone at the second end of the second body. The guide axis is transverse to the rotation axis. In use, rotation of the second arm body with respect to the first arm body changes the distance between the first bone and the second bone and rotation of the guide with respect to the first arm body rotates the first bone about a longitudinal axis of the first bone.

In another aspect, a system comprises a device. The device includes a first arm and a second arm. The first arm includes a first arm body and a guide. The first arm body extends from a first end to a second end. The guide is coupled to the second end of the first arm body. The guide is configured to be coupled to a first bone. The guide is rotatable with respect to the first arm body. The second arm includes a second arm body extending from a first end to a second end. The second arm body is coupled to the first arm body such that the second arm body is rotatable with respect to the first arm body about a rotation axis. The second arm is configured to engage a second bone at the second end of the second arm body. In use, rotation of the second arm body with respect to the first arm body changes the distance between the first bone and the second bone and rotation of the guide with respect to the first arm body rotates the first bone about a longitudinal axis of the first bone.

In another aspect, a method includes inserting a pin into a first bone and through an aperture of a guide of a device having a first arm rotatably coupled to a second arm. The guide is rotatably coupled to the first arm. The method further includes engaging the second arm with a second bone. The method further includes rotating the first arm with respect to the second arm to reduce the distance between the first bone and the second bone. The method further includes locking rotation of the guide with respect to the first arm.

In another aspect, a device includes a first arm and a second arm. The first arm includes a first arm body extending from a first end to a second and a guide coupled to the first arm body. The guide is configured to be coupled to a first bone and is rotatable with respect to the first arm body. The second arm includes a second arm body extending from a first end to a second end. The second arm body is coupled to the first arm body such that a distance between the second end of the second arm body and the guide is reduceable by a user. The second arm is configured to engage a second bone at the second end of the second arm body. In use, reduction of the distance between the second end of the second arm body and the guide reduces a distance between the first bone and the second bone and rotation of the guide with respect to the first arm body rotates the first bone about a longitudinal axis of the first bone.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

FIG. 35 is a perspective view of a locking screw and rotation lock adapter engaging the first arm body of FIG. 31.

FIG. 36 is an exploded view of some of the components of the clamping device of FIG. 27.

DETAILED DESCRIPTION

Figure 1:
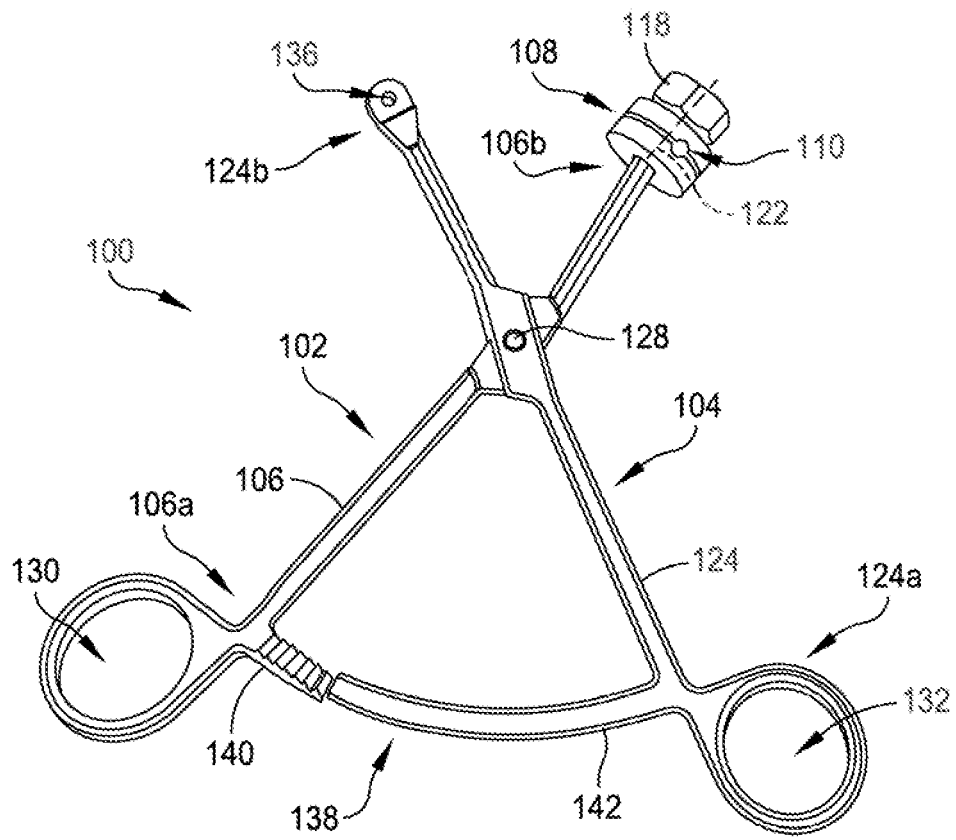
FIG. 1 is a perspective view of a clamping device according to one embodiment described herein.

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. As used herein, the term "pin" as used to describe pins inserted in a bone encompasses Kirschner wires (K-wires), bone pins, rods, screws and similar members that can be used to couple the clamping devices described herein to a bone.

The apparatuses described herein are configured for use in correction of bone deformities. Although the apparatuses can be used to correct deformities of any bone, they are particularly well-suited for use in correcting increased intermetatarsal angle between the first and second metatarsals of the foot. The apparatuses can be used in what is known as a Lapidus procedure. In addition, the apparatuses can be used to rotate the first metatarsal about a longitudinal axis of the first metatarsal (i.e., rotation in the frontal plane) to further realign the anatomy of the foot.

FIG. 1 shows a top view of an embodiment of a clamping device 100. The device 100 includes a first arm 102 and a second arm 104. The first arm 102 includes a first arm body 106 and a guide 108. The first arm body 106 extends from a first end 106a to a second end 106b. The guide 108 is coupled to the second end 106b of the first arm body 106. The guide 108 defines an aperture 110 adapted to receive a pin 112 inserted in a first bone 402, such as a first metatarsal (shown in FIG. 3). The guide 108 is rotatable with respect to the first arm body 106, as described in more detail below.

Figure 2:
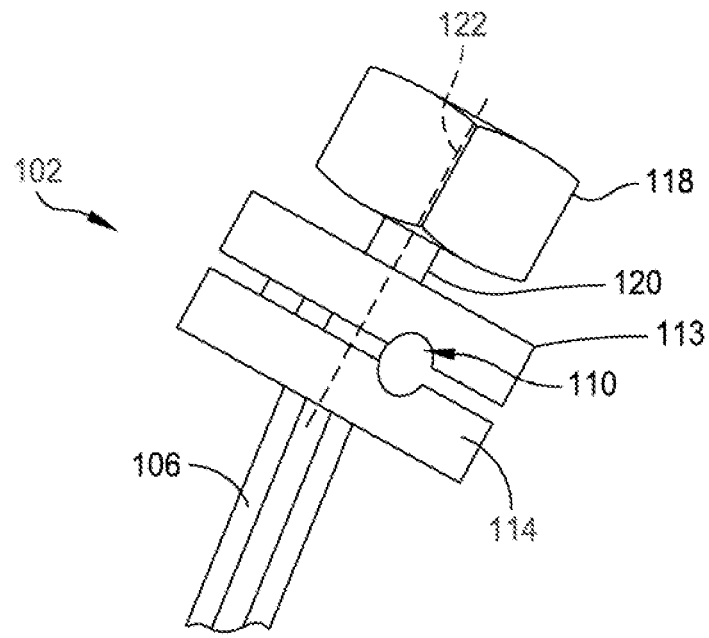
FIG. 2 is a superior view of the guide of the clamping device of FIG. 1.

As shown best in FIG. 2, in various embodiments, the guide 108 includes a first plate 113 and a second plate 114. The first 113 and second 114 plates together define the aperture 110. Further, each of the first 113 and second 114 plates define a bore transverse to the aperture 110 configured to receive a portion of the first arm body 106 passing through the bore of each of the first 113 and second 114 plates. In various embodiments, the clamping device 100 further includes a nut 118 coupled to a threaded end 120 of the first arm body 106. Rotation of the nut 118 in a first direction (e.g., clockwise) about the threaded end 120 clamps the first 113 and second 114 plates together and to the first arm body 106 to lock rotation of the guide 108 relative to the first arm body 106 and rotation of the nut 118 in a second, opposite direction (e.g., counterclockwise) about the first arm body 106 releases the rotation of the guide 108 relative to the first arm body 106. For example, the guide 108 can be rotatable about a guide axis 122 that extends along the length of the portion of the first arm body 106 that extends through the plates 113, 114.

The second arm 104 includes a second arm body 124 extending from a first end 124a to a second end 124b. The second arm body 124 is coupled to the first arm body 106 such that the second arm body 124 is rotatable with respect to the first arm body 106 about a rotation axis 126 (shown in FIG. 4) at the junction of the first arm body 106 and the second arm body 124. The rotation axis 126 can be oriented transverse to the guide axis 122 and be positioned intermediate the respective first and second ends of the first arm body 106 and the second arm body 124 such that the first 102 and second 104 arms operate in a scissor-like manner. The first arm body 106 and second arm body 124 can be coupled together using a pin or screw 128. As shown in FIG. 1, the first arm body 106 can define a finger hole 130 and the second arm body 124 can define a finger hole 132 to allow a user to operate the device 100.

The second arm 104 is configured to engage a second bone 404 (shown in FIG. 3) at the second end 124b of the second arm body 124. As will be described further herein, in use, rotation of the second arm body 124 with respect to the first arm body 106 changes (e.g., reduces) the distance between the first bone 402 and the second bone 404 to reduce the hallux valgus angle and rotation of the guide 108 with respect to the first arm body 106 rotates the first bone 402, for example about the longitudinal axis of the second bone (i.e., rotation of the first bone 402 in the frontal anatomic plane).

Figure 3:
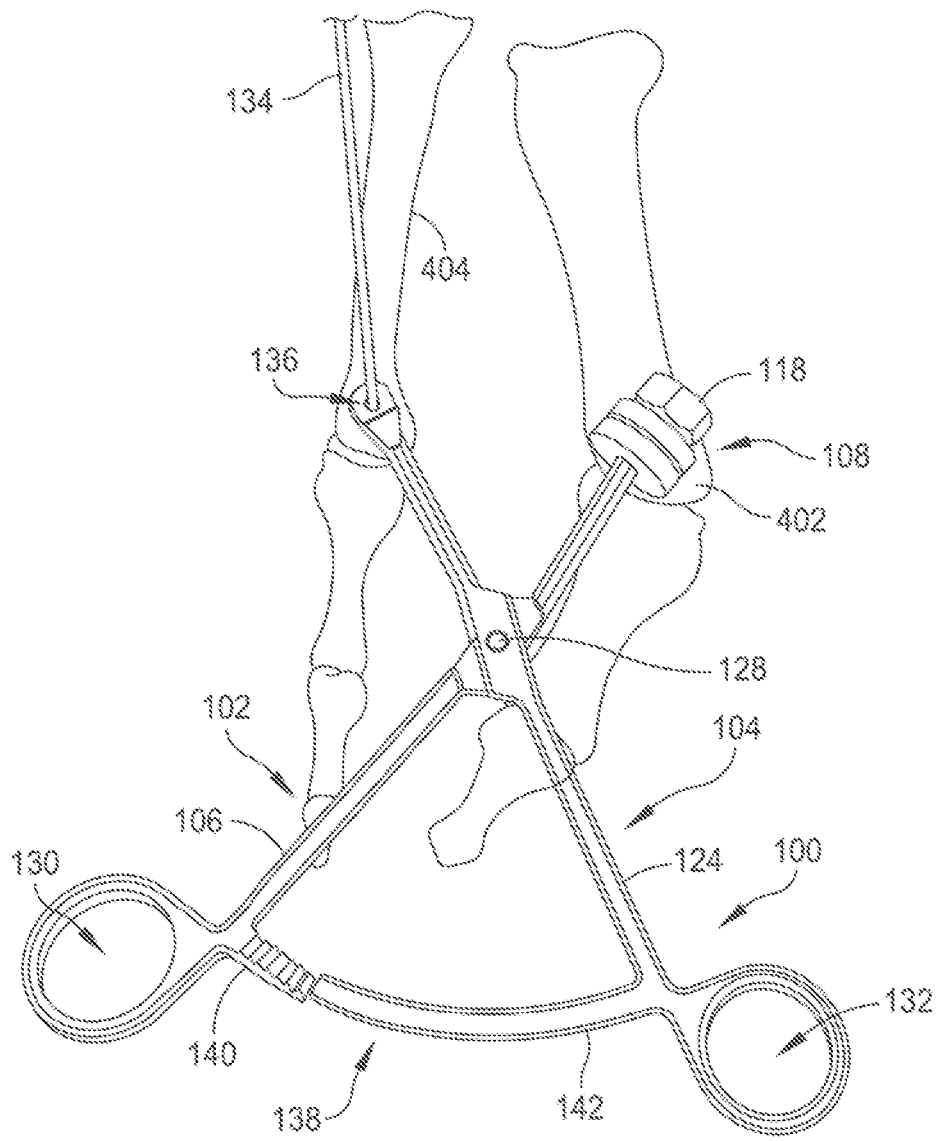
FIG. 3 is a superior view of the clamping device of FIG. 1 in use to reduce a hallux valgus angle.

In some embodiments, the second arm body 124 engages the second bone 404 via a pin 134, as shown in FIG. 3. In such embodiments, the second arm body includes a second aperture 136 at the second end 124b of the second arm body 124. The second aperture 136 is adapted to receive the pin 134 to couple the second arm body 124 to the second bone. In other embodiments, as will be described herein, the second arm body 124 may couple to the second bone 404 via a hook that contacts the lateral side of the second bone 404.

The clamping device 100 can further include a locking mechanism 138 configured to lock the position of the first arm body 106 relative to the second arm body 124. In some embodiments, the locking mechanism includes a first locking arm 140 extending from the first arm body 106 and a second locking arm 142 extending from the second arm body 124. The first 140 and second 142 locking arms each include locking teeth configured to engage with one another to at least temporarily lock the positions of the first arm body 106 and the second arm body 124.

FIGS. 3-7 show steps in a method of using the device 100 to correct (e.g., reduce) a hallux valgus angle. As shown in FIG. 3, the pin 134 is inserted into the second bone 404 (e.g., the second metatarsal). The second aperture 136 of the second arm body 124 is passed over the pin 134 to couple the second arm body 124 to the second bone 404.

Figure 4:
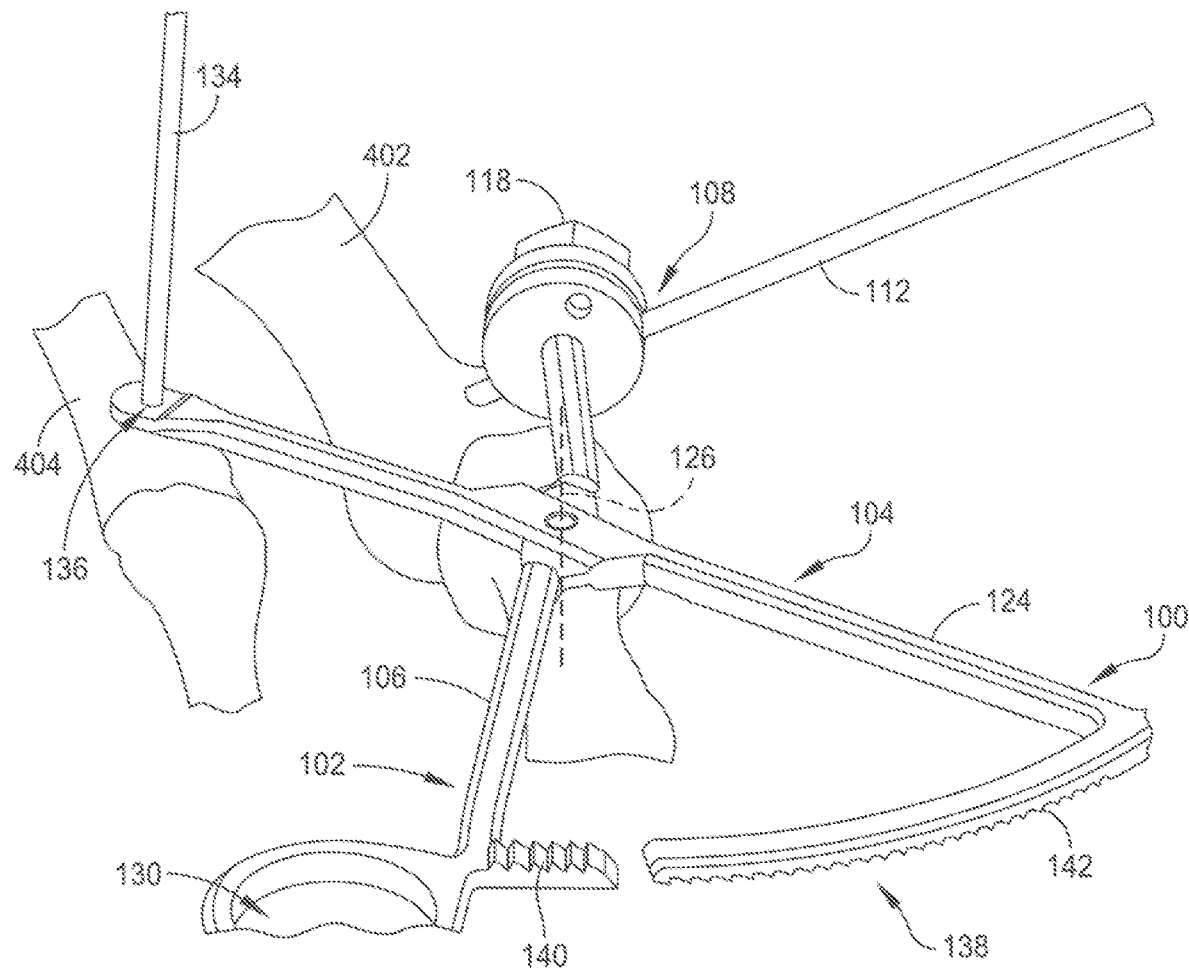
FIG. 4 is a perspective view of the clamping device of FIG. 1 in use and after insertion of a pin through the aperture of the guide.

Turning to FIG. 4, a pin 112 is inserted through the aperture 110 in the guide 108 and into the first bone 402 (e.g., the first metatarsal). Insertion of the pin 112 can be guided by fluoroscopy or another imaging modality to allow the pin 112 to be inserted at a desired orientation. It should be understood that the steps of inserting the pins 112, 134 and coupling the device 100 to the pins 112, 134 can be performed in any desired order. For example, the pin 112 could first be inserted into the first bone 402. The guide 108 could then be placed over the first pin 112 before the second pin 134 is inserted through the aperture 136 and into the second bone 404.

Figure 5:
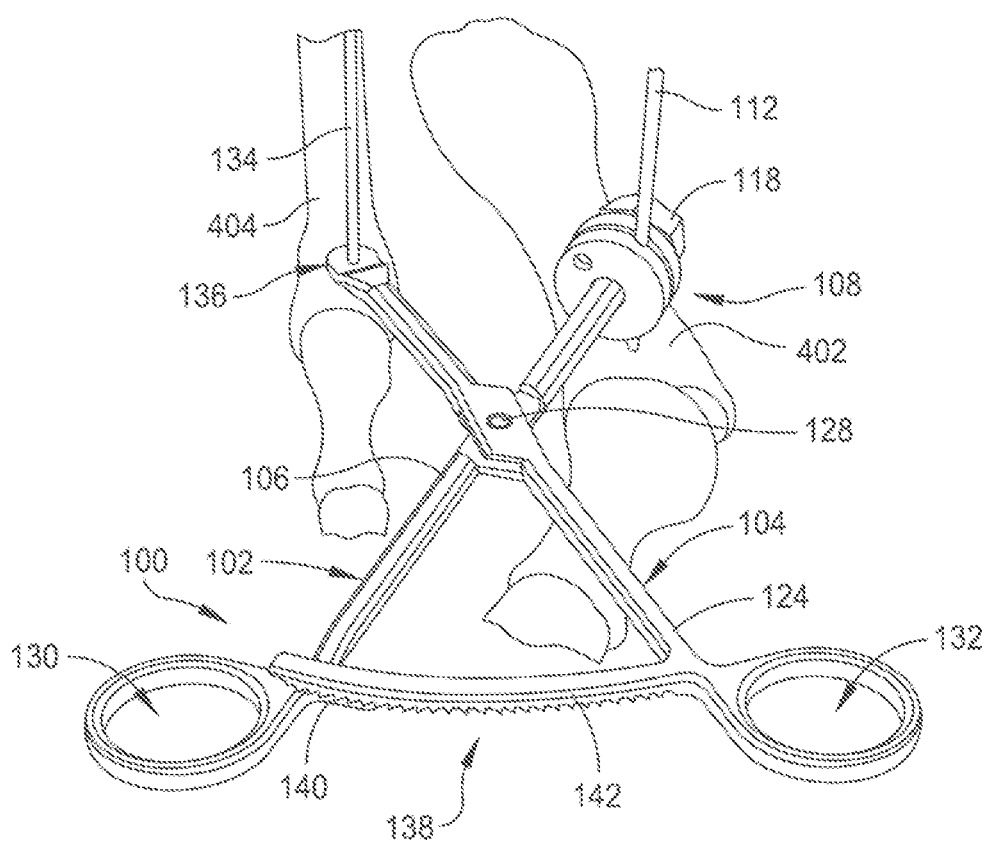
FIG. 5 is a perspective view of the clamping device of FIG. 1 in use and after frontal plane rotation of the first metatarsal.
Figure 6:
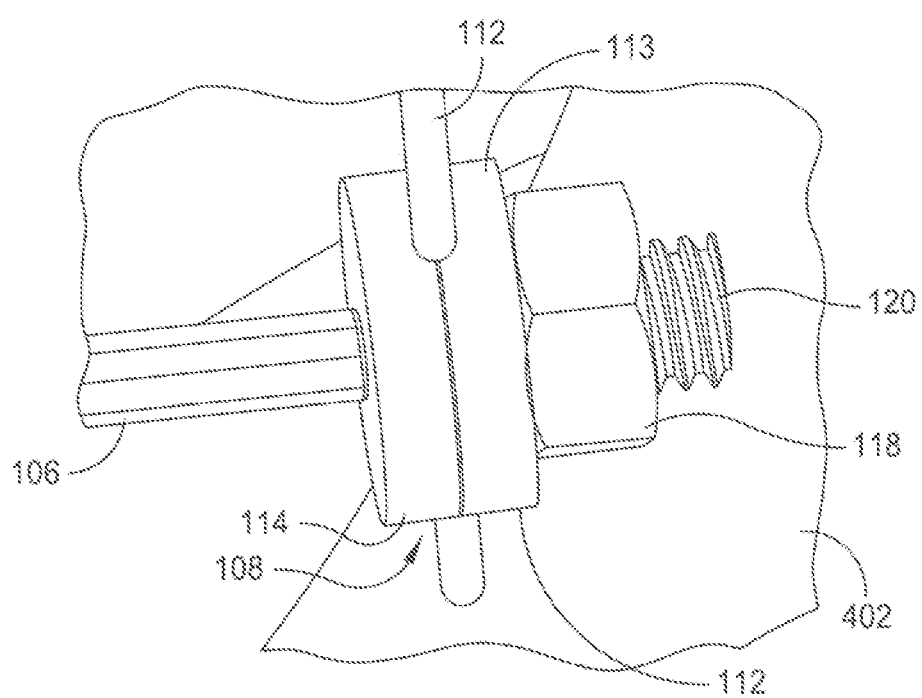
FIG. 6 is a detail view of the guide after locking of rotation of the guide.

As shown in the transition from FIG. 4 to FIG. 5, the first bone 402 is then rotated in the frontal plane (i.e., about a longitudinal axis of the first bone 402), as shown in FIGS. 14A and 14B and described in more detail below. In some embodiments, the surgeon can use the pin 112 as a lever to rotate the first bone 402. As the surgeon rotates the first bone 402, the guide 108 rotates around the guide axis 122. With the first bone 402 in the desired rotational position, the surgeon tightens the nut 118 to lock rotation of the guide 108 and, thereby, rotation of the first bone 402.

Figure 7:
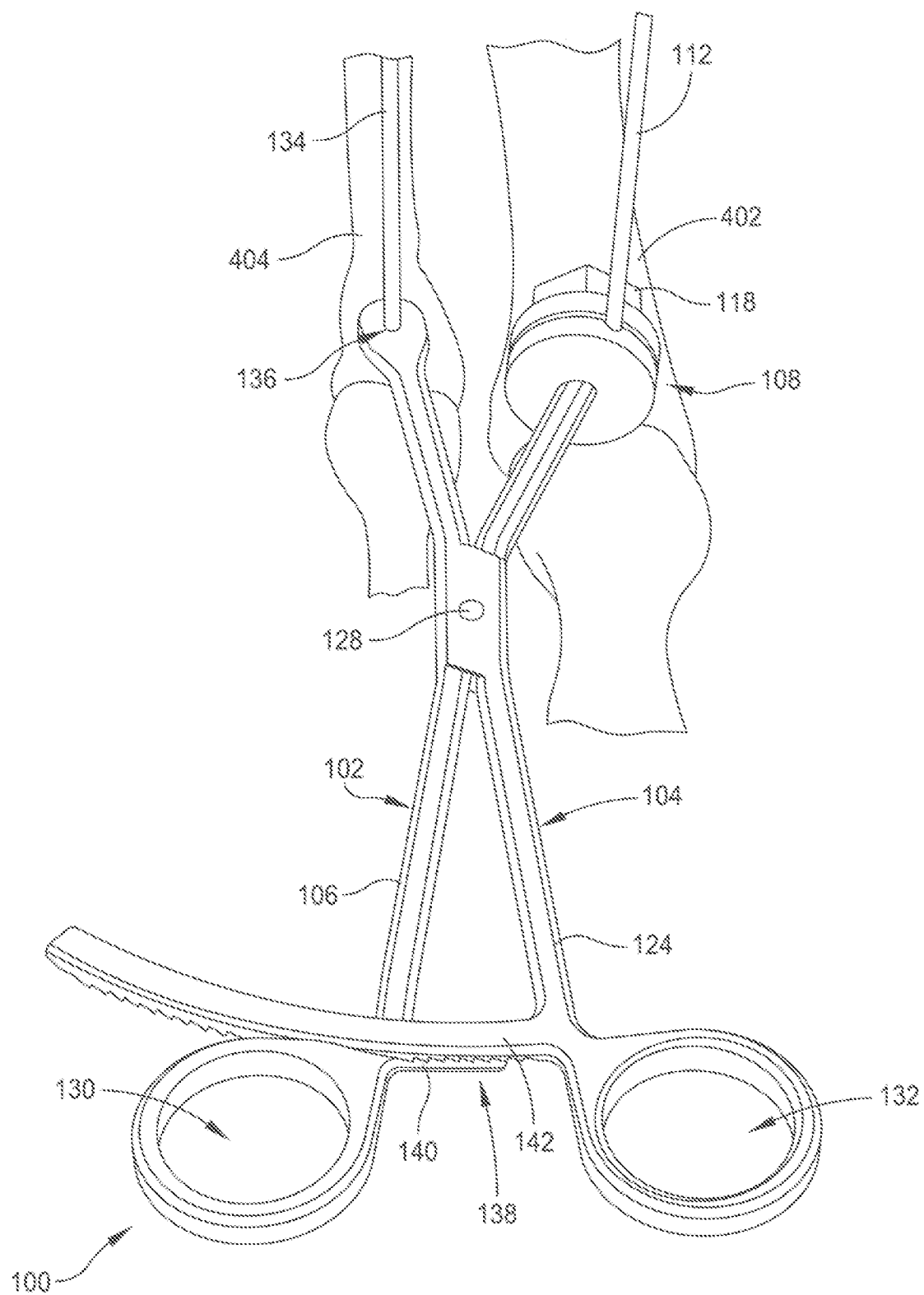
FIG. 7 is a detail view of the clamping device in use and after reduction of the hallux valgus angle.

With the guide 108 and the first bone 402 in the desired rotational position and with rotation of the guide 108 locked, the surgeon can compress the first arm body 106 and the second arm body 124 together to reduce the distance between the first bone 402 and the second bone 404. The surgeon continues to compress the first arm body 106 and the second arm body 124 until the first bone 402 and the second bone 404 are in the desired position, as shown in FIG. 7, and the hallux valgus angle is reduced. It should be understood that the rotation of the guide 108 can be locked before, during, or after reducing the hallux valgus angle. For example, in some procedures, the surgeon may allow the guide 108 to be rotatable about the guide axis 122 while reducing the hallux valgus angle such that the first bone 402 (e.g., the first metatarsal) is able to rotate in the frontal plane (e.g., about a longitudinal axis of the bone) while the hallux valgus angle is reduced. This may allow for the natural anatomy of the bones of the foot, for example the contacting surfaces of the first metatarsal and tarsal bones, to cause rotation of the bone in the frontal plane toward a more natural position. In some embodiments, rotation of the guide 108 is unlocked during a first portion of the reduction of the hallux valgus angle and rotation of the guide 108 is then locked before completing reduction of the hallux valgus angle.

With the hallux valgus angle reduced as desired, the locking mechanism 138 can maintain the relative positions of the first arm body 106 and the second arm body 124 to maintain the position of the first bone 402 and the second bone 404. A plate, screw, suture, or other means of fixation can then be applied to the bones to hold them in position before removing the pins 112, 134 and device 100. For example, a plate can be secured to the first metatarsal and the proximal phalanx to secure the first metatarsal in position.

Figure 8:
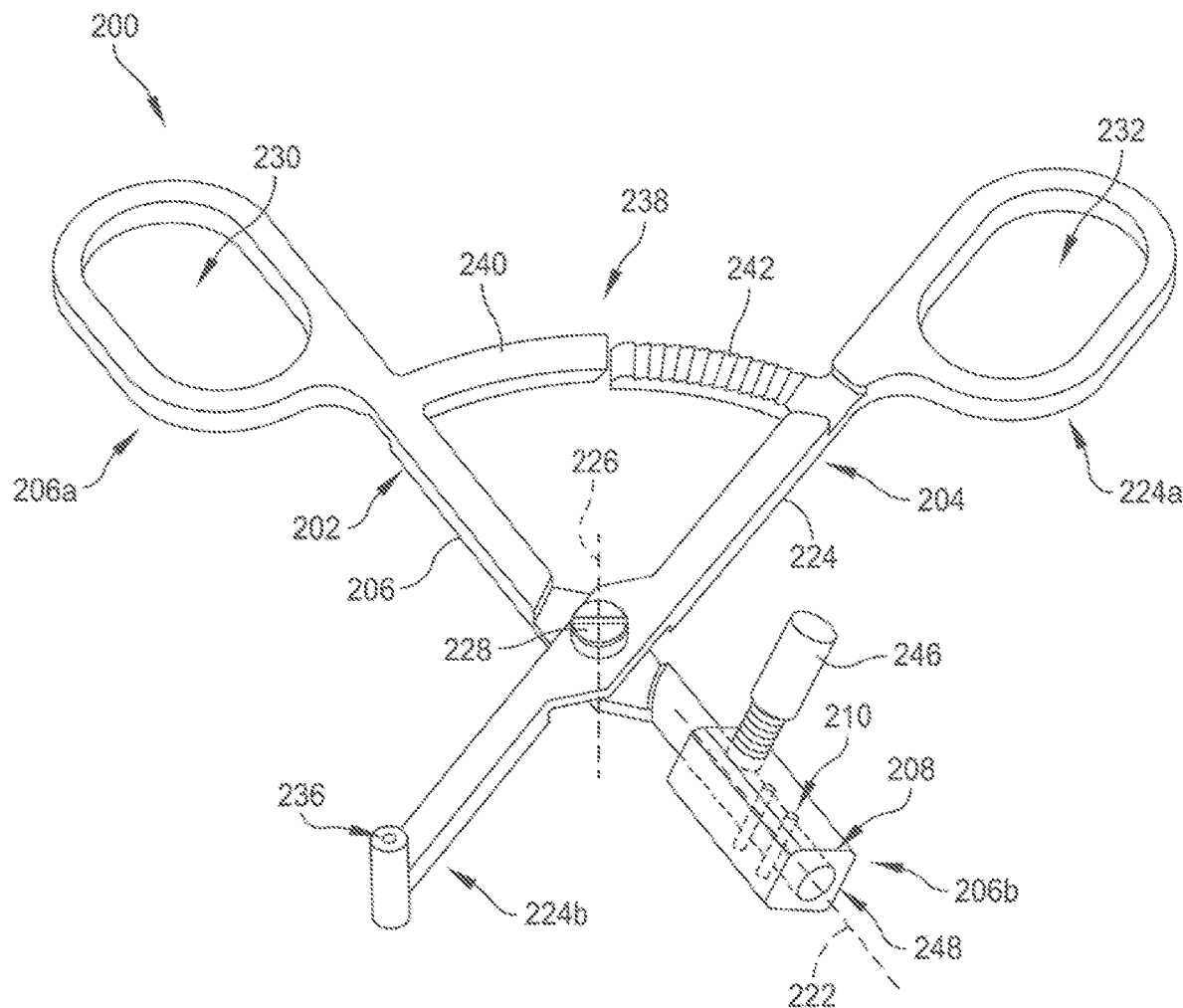
FIG. 8 is a perspective view of a clamping device according to another embodiment described herein.
Figure 9:
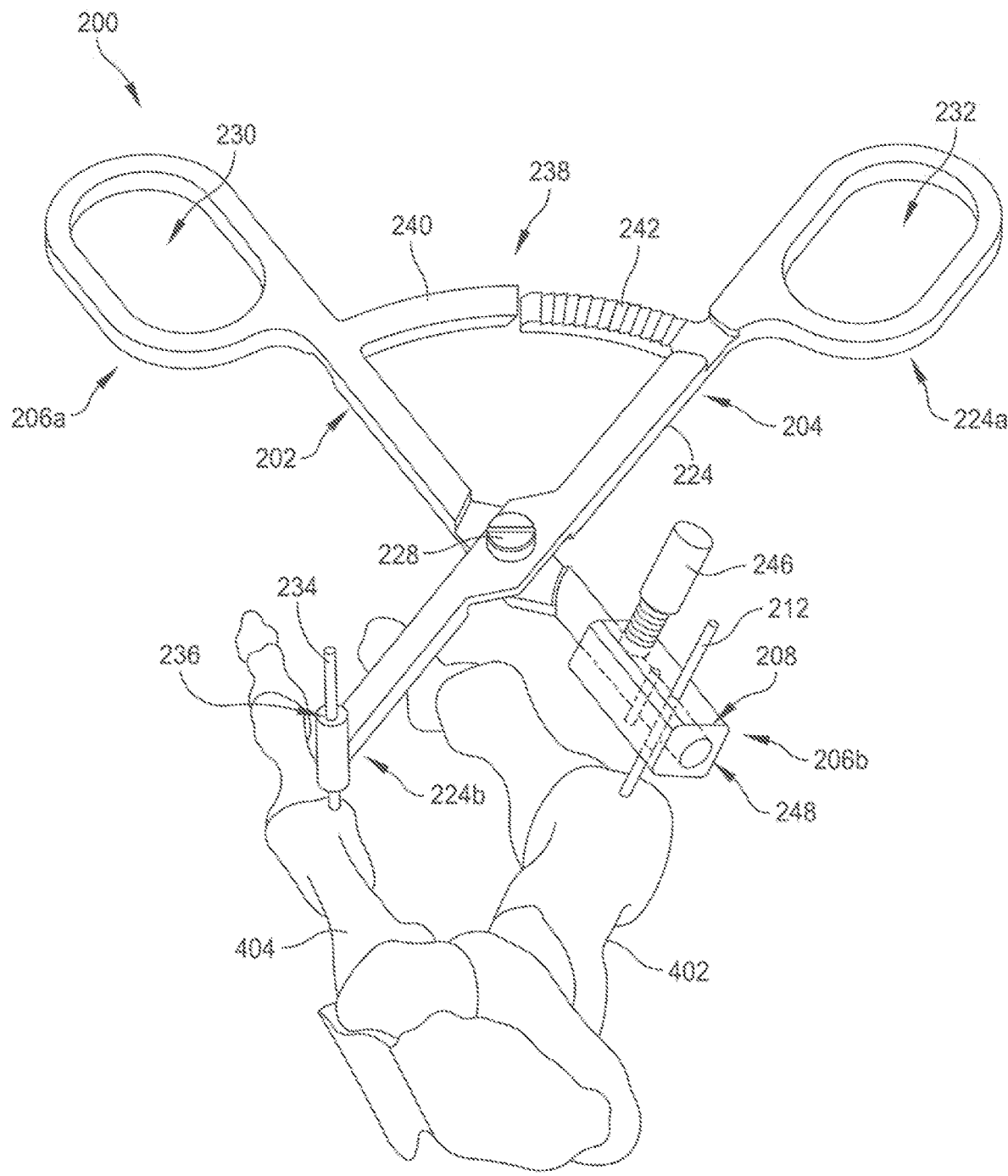
FIG. 9 is a perspective view of the clamping device of FIG. 8 in use and prior to correction of the hallux valgus angle.

FIG. 8 shows a perspective view of another embodiment of a clamping device 200. The clamping device 200 includes a first arm 202 and a second arm 204. The first arm 202 includes a first arm body 206, a guide 208, and a locking screw 246. The first arm body 206 extends from a first end 206a to a second end 206b. The guide 208 is coupled to the first arm body 206 at the second end 206b. The guide 208 includes a first aperture 210 adapted to receive a pin 212 (FIG. 9) inserted in a first bone 402 (FIG. 9). The guide 208 is rotatable with respect to the first arm body 206 about a guide axis 222.

The locking screw 246 is coupled to the guide 208. Rotation of the locking screw 246 in a first direction (e.g., clockwise) locks rotation of the guide 208 with respect to the first arm body 206 and rotation of the locking screw 246 in a second direction (e.g., counter-clockwise) releases rotation of the guide 208 with respect to the first arm body 206. In some embodiments, the guide 208 defines a bore 248 and a portion of the first arm body 206 extends through the bore 248 and the locking screw 246 is a set screw configured to engage the portion of the first arm body 206 that extends through the guide 208 to restrict rotation of the guide 208. It should be understood that the clamping devices described herein can include alternative or additional mechanisms for locking and releasing rotation of the guide. As shown best in FIG. 14, the first arm body 206 can include a circumferential groove 262 extending around the first arm body 206. The guide 208 can include a hole for insertion of a pin 264 such that the pin 264 is at least partially disposed in the groove 262. During assembly, the pin 264 is inserted into the hole and the groove 262 to axially position the guide 208 and prevent inadvertent removal of the guide 208 from the first arm body 206.

The second arm 204 includes a second arm body 224 extending from a first end 204a to a second end 204b. The second arm body 224 is coupled to the first arm body 206 such that the second arm body 224 is rotatable with respect to the first arm body 206 about a rotation axis 226. The guide axis 222 is transverse to the rotation axis 226. In some embodiments, the transverse guide axis 222 and rotation axis 226 are perpendicular to one another. The second arm 204 includes a second aperture 236 at the second end 224b of the second arm body 224. The second aperture 236 is adapted to receive a pin 234 (FIG. 9) inserted in a second bone 404. In use, rotation of the second arm body 224 with respect to the first arm body 206 changes the distance between the first bone 402 and the second bone 404 and rotation of the guide 208 with respect to the first arm body 206 rotates the first bone 402 (e.g., in the frontal plane). The rotation axis 226 can be positioned intermediate the respective first and second ends of the first arm body 206 and the second arm body 224 such that the first 202 and second 204 arms operate in a scissor-like manner. The first arm body 206 and second arm body 224 can be coupled together using a pin or screw 228. As shown in FIG. 8, the first arm body 206 can define a finger hole 230 and the second arm body 224 can define a finger hole 232 to allow a user to operate the device 200.

The clamping device 200 can further include a locking mechanism 238 configured to lock the position of the first arm body 206 relative to the second arm body 224. In some embodiments, the locking mechanism 238 includes a first locking arm 240 extending from the first arm body 206 and a second locking arm 242 extending from the second arm body 224. The first 240 and second 242 locking arms each include locking teeth configured to engage with one another to at least temporarily lock the positions of the first arm body 206 and the second arm body 224.

Figure 10:
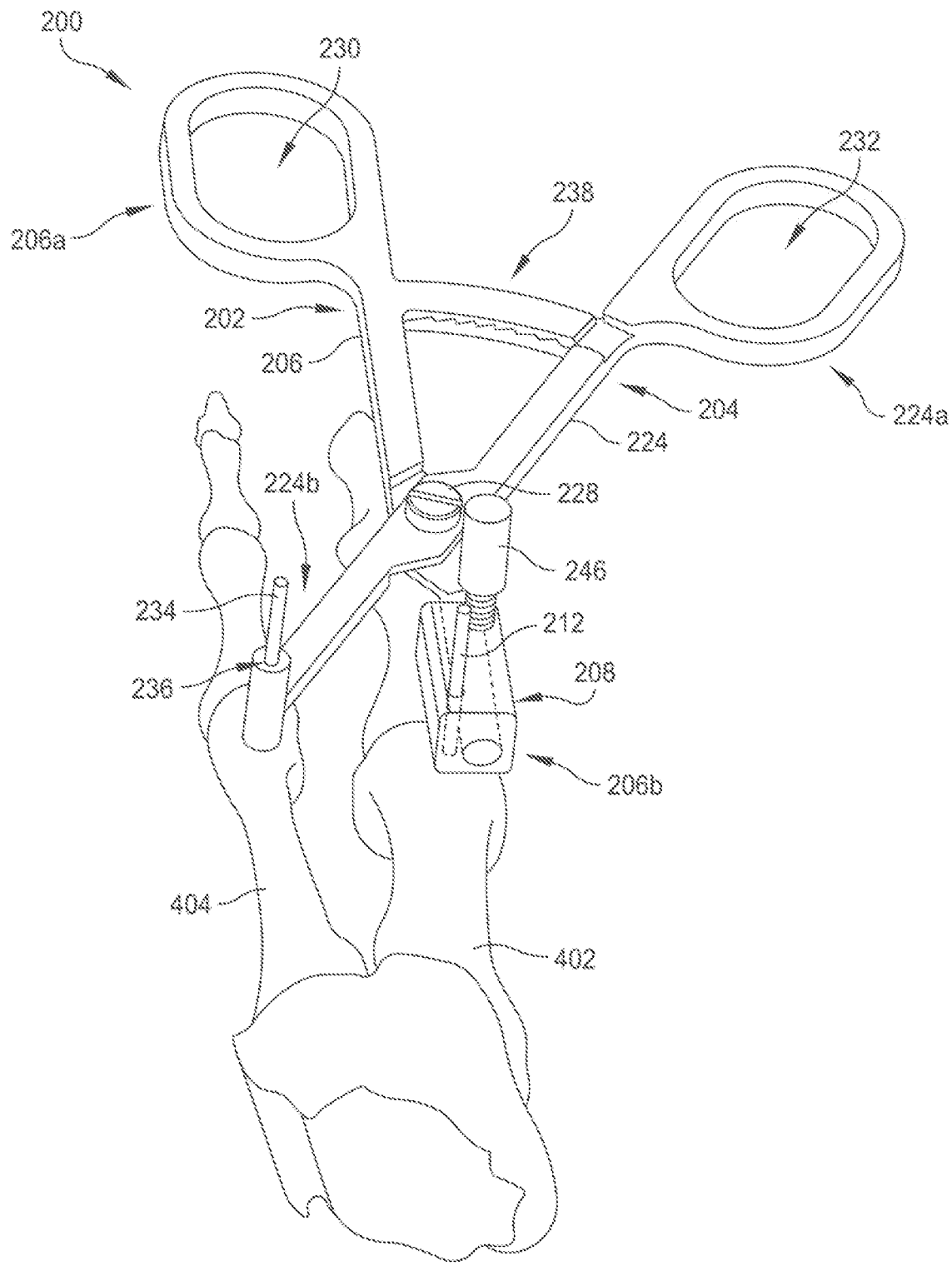
FIG. 10 is a perspective view of the clamping device of FIG. 8 in use and after correction of the hallux valgus angle.

FIGS. 9 and 10 show the clamping device 200 in use. In many aspects, the steps of using the clamping device 200 can be similar to the steps of using clamping device 100, as described above. As shown in FIG. 9, a pin 234 is inserted into the second bone 404 (e.g., a second metatarsal) and the second arm 204 is coupled to the second bone 404 by passing the pin 234 through the second aperture 236 in the second arm body 224. A pin 212 is inserted through the first aperture 210 in the guide 208 and into the first bone 402 (e.g., a first metatarsal). It should be understood that the steps of inserting the pins and coupling the device 200 to the pins can be performed in any desired order. For example, the pin 212 could first be inserted into the first bone 402. The guide 208 could then be placed over the first pin 212 before the second pin 234 is inserted through the aperture 236 and into the second bone 404.

As described above, the first bone 402 is rotated in the frontal plane (i.e., about a longitudinal axis of the first bone 402), as shown in FIGS. 14A and 14B and described in more detail herein. Rotation guide 208 rotates with respect to the first arm body 206 as the first bone 402 is rotated. With the first bone 402 in the desired rotational orientation, the surgeon can rotate the locking screw 246 to lock rotation of the guide 208.

Further, the surgeon can also squeeze the first end 206a of the first arm body 206 toward the first end 224a of the second arm body 224. In so doing, the second end 206b of the first arm body 206 is brought nearer to the second end 224b of the second arm body 224, thereby reducing the hallux valgus angle. It should be understood that the rotation of the guide 208 can be locked before or after reducing the hallux valgus angle. For example, in some procedures, the surgeon may allow the guide 208 to be rotatable about the guide axis 222 while reducing the hallux valgus angle such that the first bone 402 (e.g., the first metatarsal) is able to rotate in the frontal plane (e.g., about a longitudinal axis of the bone) while the hallux valgus angle is reduced. This may allow for the natural anatomy of the bones of the foot, for example the contacting surfaces of the first metatarsal and tarsal bones, to cause rotation of the bone in the frontal plane toward a more natural position. In some embodiments, rotation of the guide 208 is unlocked during a first portion of the reduction of the hallux valgus angle and rotation of the guide 208 is then locked before completing reduction of the hallux valgus angle.

With the hallux valgus reduced as desired, the locking mechanism 238 can maintain the relative positions of the first arm body 206 and the second arm body 224 to maintain the position of the first bone 402 and the second bone 404. A plate, screw, suture, or other means of fixation can then be applied to the bones to hold them in position before removing the pin 212, 234 and clamping device 200.

Figure 11:
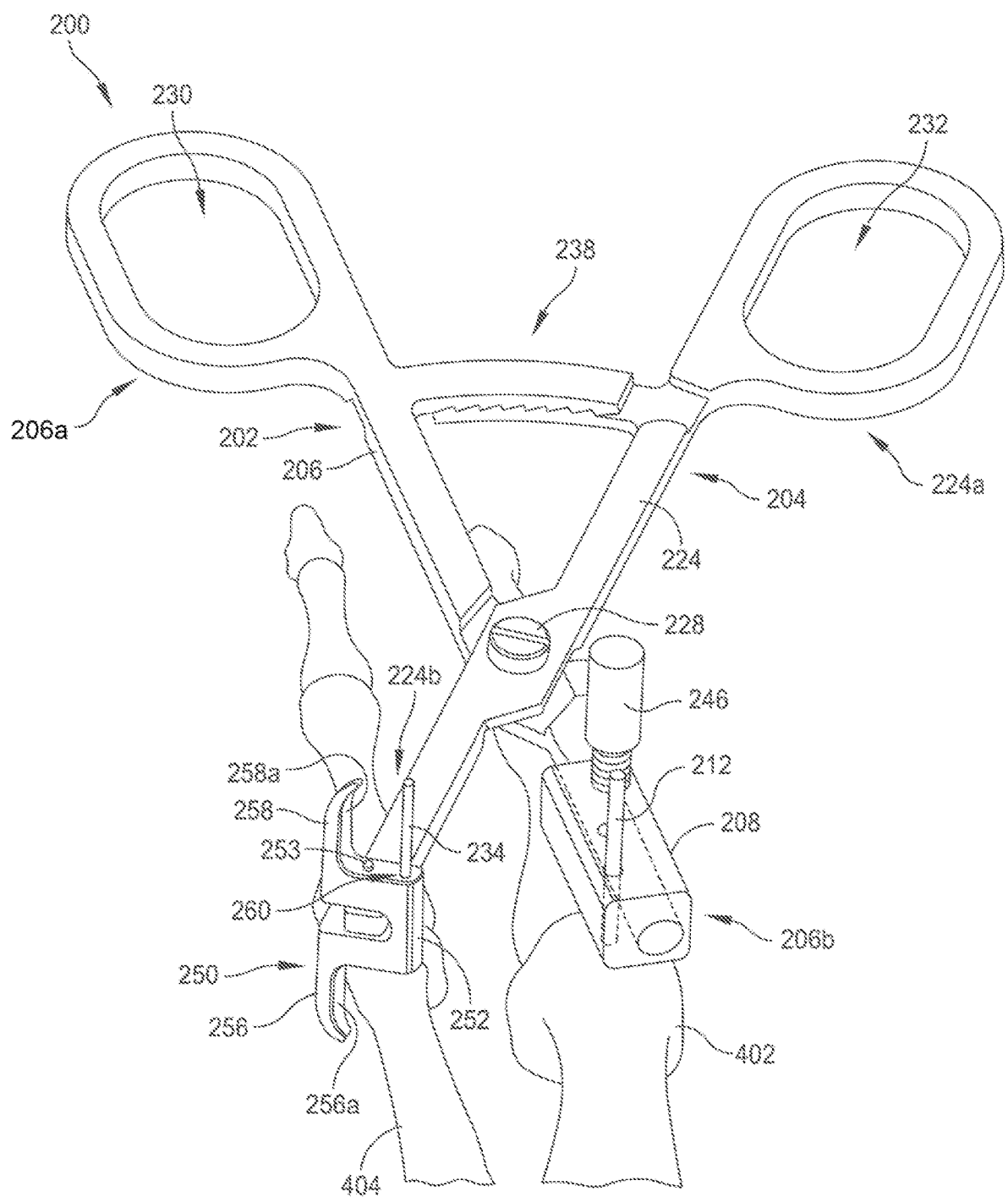
FIG. 11 is a perspective of a clamping device according to another embodiment in use.
Figure 12:
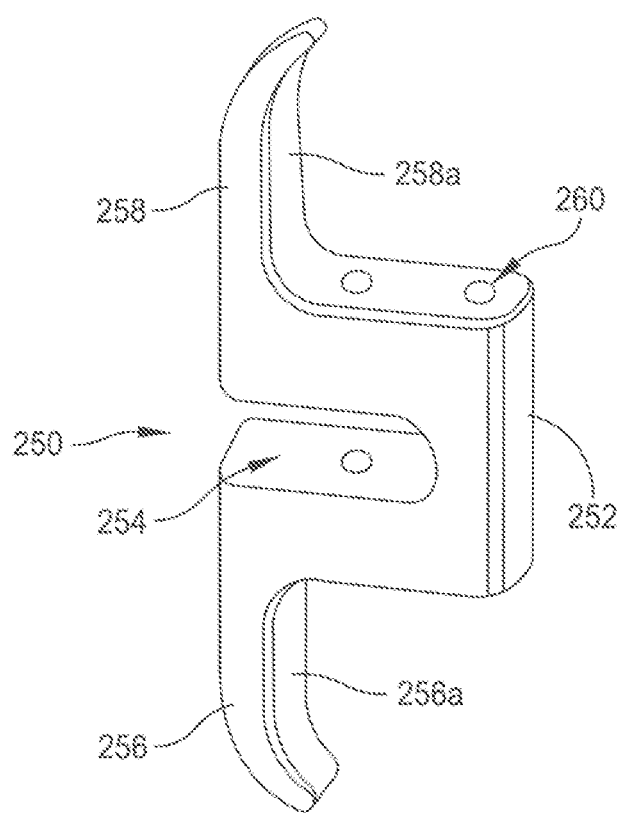
FIG. 12 is a perspective view of the engagement member of the clamping device of FIG. 11.

FIG. 11 shows another embodiment of the clamping device 200. In this embodiment, an engagement member 250 is coupled to the second end 224b of the second arm body 224. The engagement member 250 is configured to engage the second bone 404 during a procedure to allow the reduction of the hallux valgus angle, as described above. The engagement member 250 (shown in detail in FIG. 12) includes an engagement body 252 defining an aperture 254 configured to receive a portion of the second arm body 224. In some embodiments, the aperture 254 can be opened on one side, as shown in FIG. 12. In other embodiments (shown, for example, in FIG. 14), the aperture 254 is enclosed on all sides. A pin 253 (shown in FIG. 11) can couple the engagement body 252 to the second arm body 224. In other embodiments, other methods of coupling the engagement body 252 to the second arm body 224 such as screws or other means can be used. In some embodiments, the engagement body 252 is able to rotate about an axis defined by the pin 253 (or other attachment means) relative to the second arm body 224. This may allow the engagement body 252 to rotate during reduction of the intermetatarsal angle.

The engagement member 250 further includes a first hook 256 extending in a first direction from the engagement body 252 and a second hook 258 extending in a second, opposite direction from the engagement body 252. The hooks 256, 258 are configured to engage the lateral side of the second bone 404. Including both the first 256 and second 258 hooks allows the clamping device 200 to be used on both the left and right foot as the clamping device 200 can be turned over to allow for use on either foot. The hooks 256, 258 can each include a concave surface 256a, 258a configured to engage and conform to the second bone 404.

In some embodiments, the engagement body 252 further defines an aperture 260 extending through the engagement body 252 and configured to receive a pin 234 (e.g., a k-wire, Steinmann pin, etc.). The pin 234 (shown in FIG. 11) can be inserted through the aperture 260 and into the second bone 404, as described above with respect to the embodiment of FIGS. 8-10. Providing an engagement member 250 with hooks 256, 258 and with the aperture 260 for receiving the pin 234 allows the surgeon to determine whether the second bone (e.g., second metatarsal) is sufficiently large to receive the pin 234 for engaging the second arm 204 to the second bone 404. If the surgeon determines that the second bone 404 is not large enough, or otherwise determines that the use of the pin 234 is not appropriate, one of the hooks 256, 258 can be used to engage the second arm 204 to the second bone 404.

It should be understood that an engagement member similar to the engagement member 250 shown in FIG. 11 can also be used in conjunction with the clamping device 100 shown in FIGS. 1-7.

Figure 13:
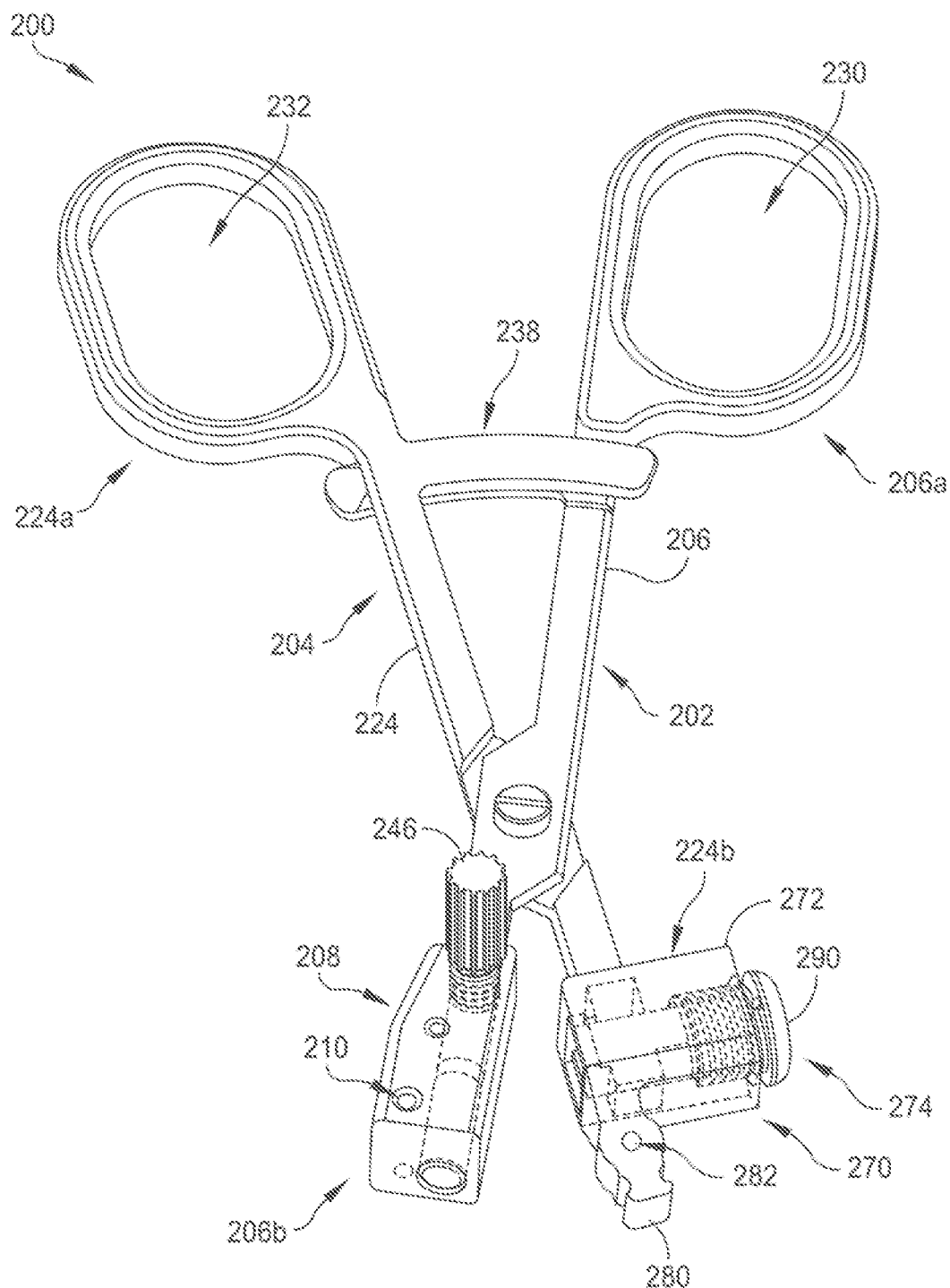
FIG. 13 is a perspective view of a clamping device, according to an embodiment, in which the clamping device includes a coupler.
Figure 14:
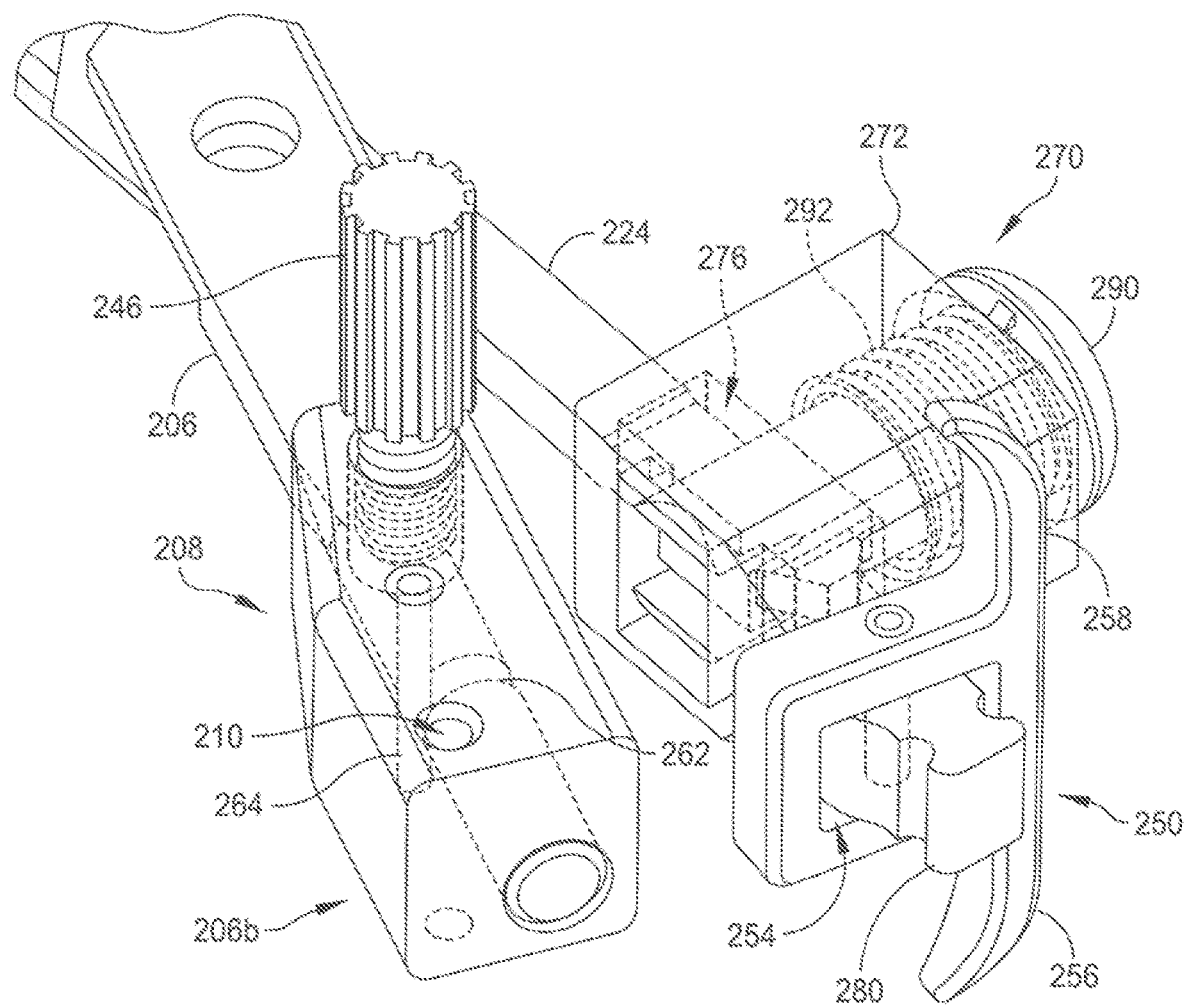
FIG. 14 is a detail perspective view of the guide, coupler, and engagement member of the device of FIG. 13.
Figure 16:
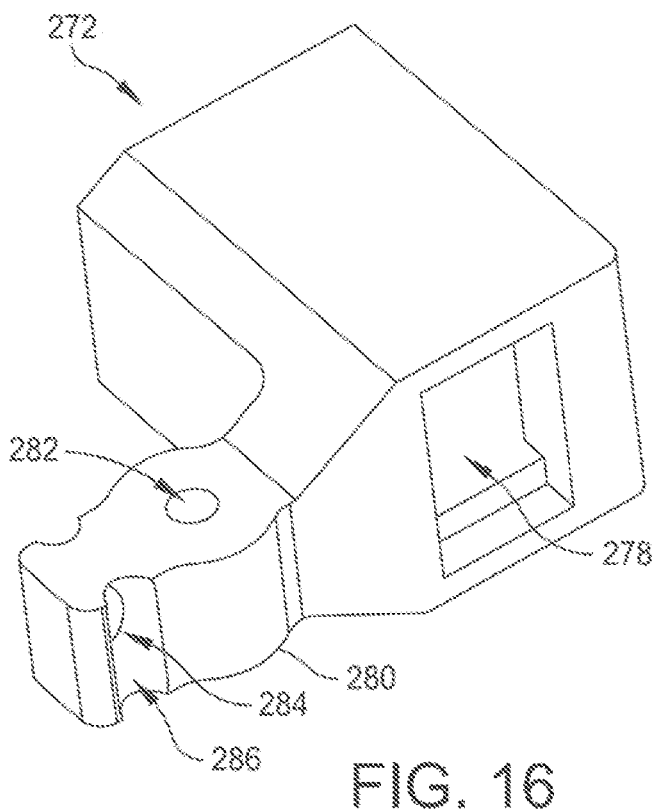
FIG. 16 is a perspective view of the coupler body of the coupler of FIG. 14.

As shown in FIGS. 13 and 14, in some embodiments, the device 200 includes a coupler 270 to attach the engagement member 250 to the second arm body 224. The coupler 270 includes a coupler body 272 and a release mechanism 274. The coupler body 272 is releasably attached to the second arm body 224. As shown in FIG. 14, the coupler body 272 defines a bore 276 for receiving a portion of the second arm body 224. As shown in FIG. 16, the coupler body 272 further defines a passage 278 for receiving a portion of the release mechanism 274, as described in more detail herein. The coupler body 272 includes a projection 280 for coupling to the engagement member 250 and to the first 402 and second 404 bones. The projection 280 defines an aperture 282 configured to receive a pin 234 to couple the coupler 270 to the second bone 404 and/or the engagement member 250 (as shown in FIG. 14). In some embodiments, the central axis of the aperture 282 is parallel to the rotation axis 226.

Figure 16A:
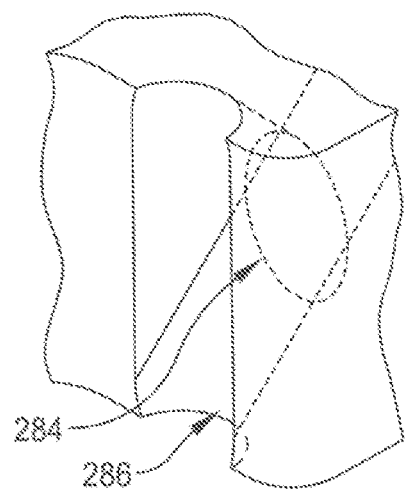
FIG. 16A is a detail view showing the cross aperture in the coupler body of FIG. 16.
Figure 17:
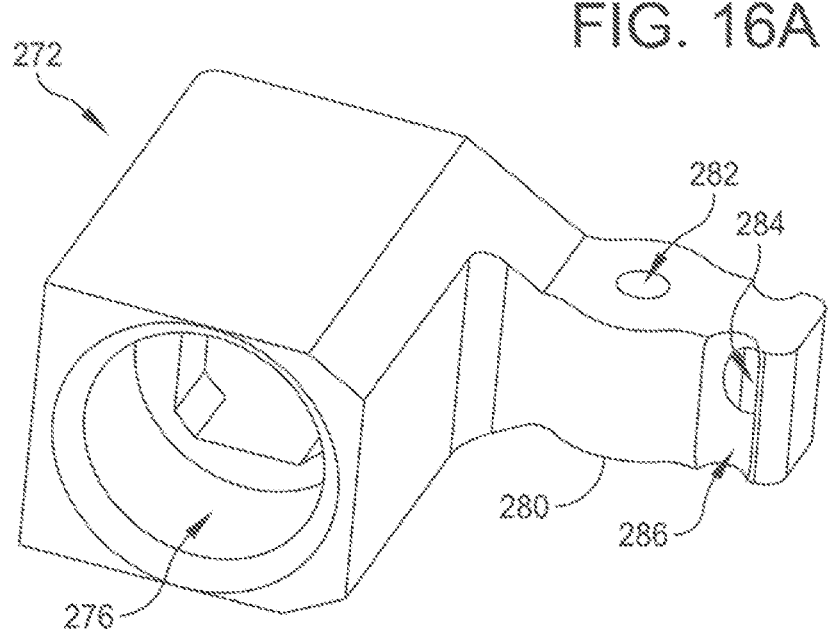
FIG. 17 is a second perspective view of the coupler body of the coupler of FIG. 14.

The projection 280 further defines a cross aperture 284 configured to guide insertion of a pin into the first bone 402, as described in further detail herein. In some embodiments, the cross aperture 284 is oblong or oval such that the pin can be inserted through the cross aperture 284 at an oblique angle, for example at an oblique angle to the aperture 282 and at an oblique angle to the sagittal plane. As shown best in FIG. 16A, the cross aperture 284 can open into generally v-shaped recesses 286 on each side of the cross aperture 284. The v-shaped recesses 286 can be used to guide the insertion of the pin into the first bone 402, as described in more detail herein. By including a v-shaped recess 286 on each side of the cross-aperture 284, the device 200 can be used on both the left and right foot. In some embodiments, the coupler body 272 includes more than one cross aperture 284, with each cross aperture 284 spaced axially along the projection 280. This may allow a surgeon to choose the location for the oblique pin based on the patient's anatomy.

Figure 15:
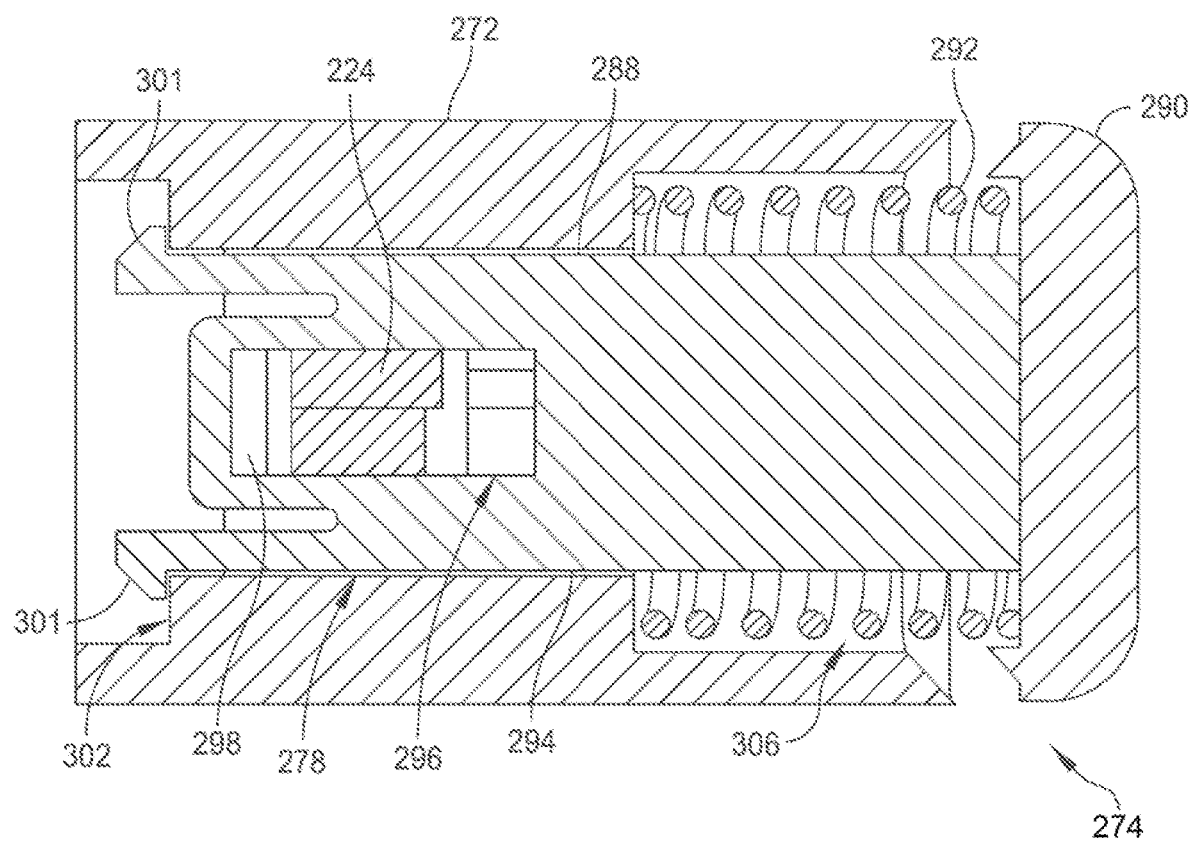
FIG. 15 is a cross-sectional view of the coupler of FIG. 14.
Figure 18:
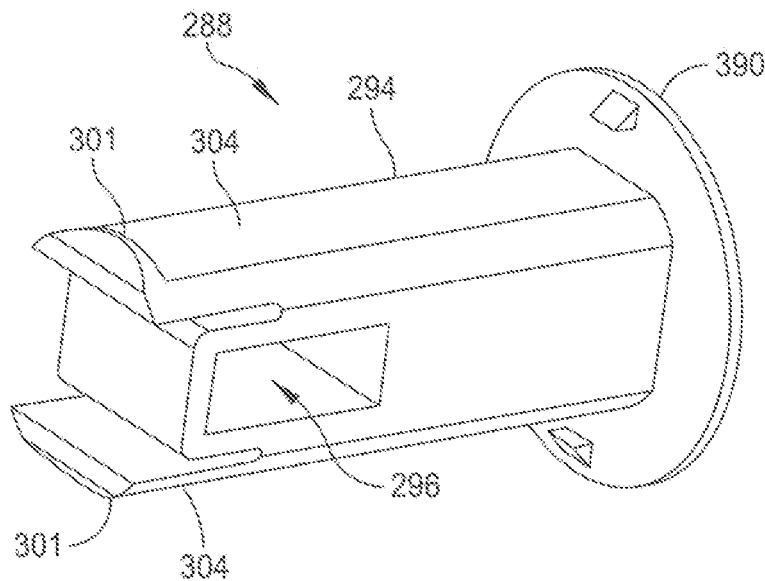
FIG. 18 is a perspective view of the slide and button of the coupler of FIG. 14.
Figure 19:
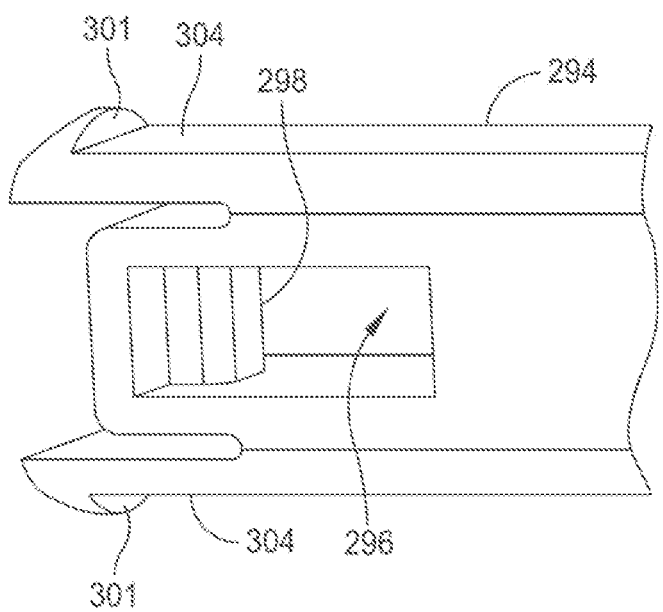
FIG. 19 is a detail view of an end of the slide of FIG. 18.
Figure 20:
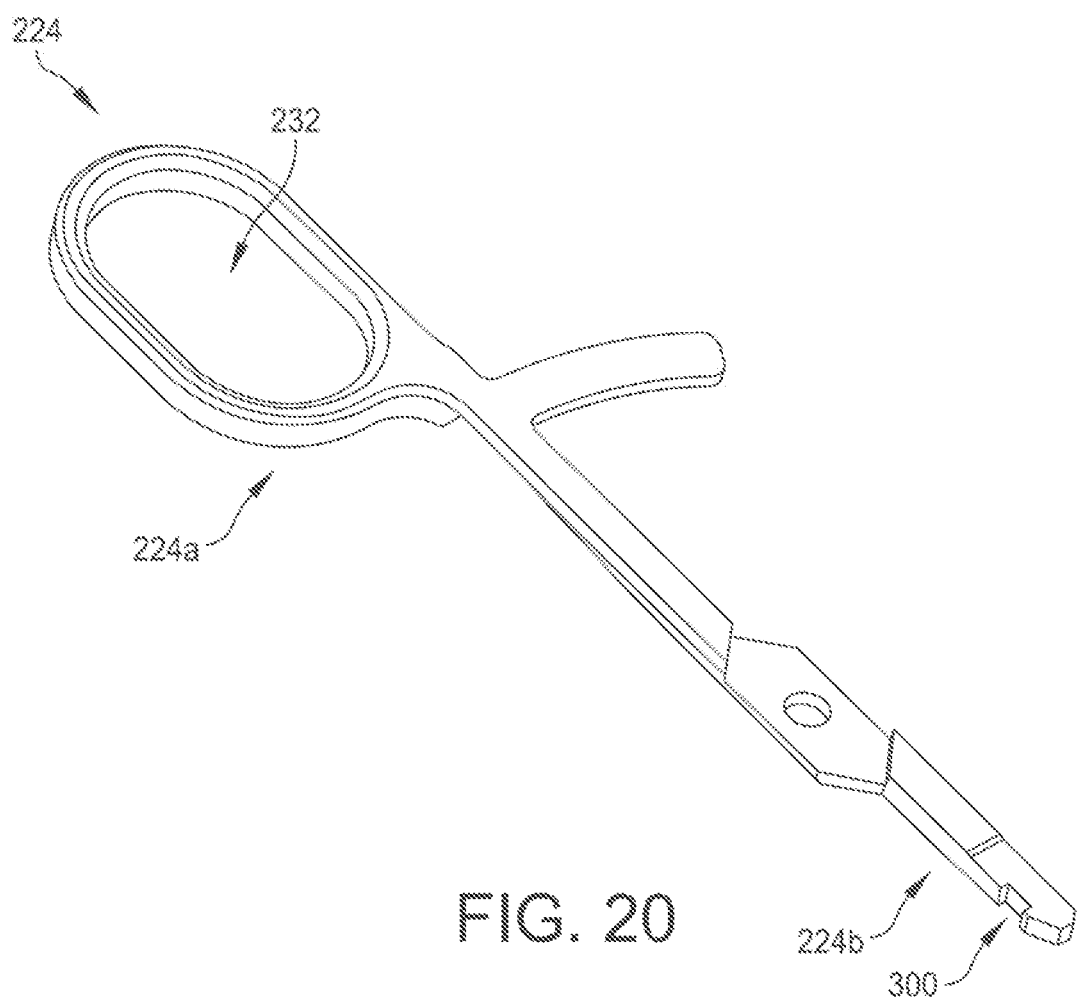
FIG. 20 is a perspective view of the second arm body of the device of FIG. 13.
Figure 21:
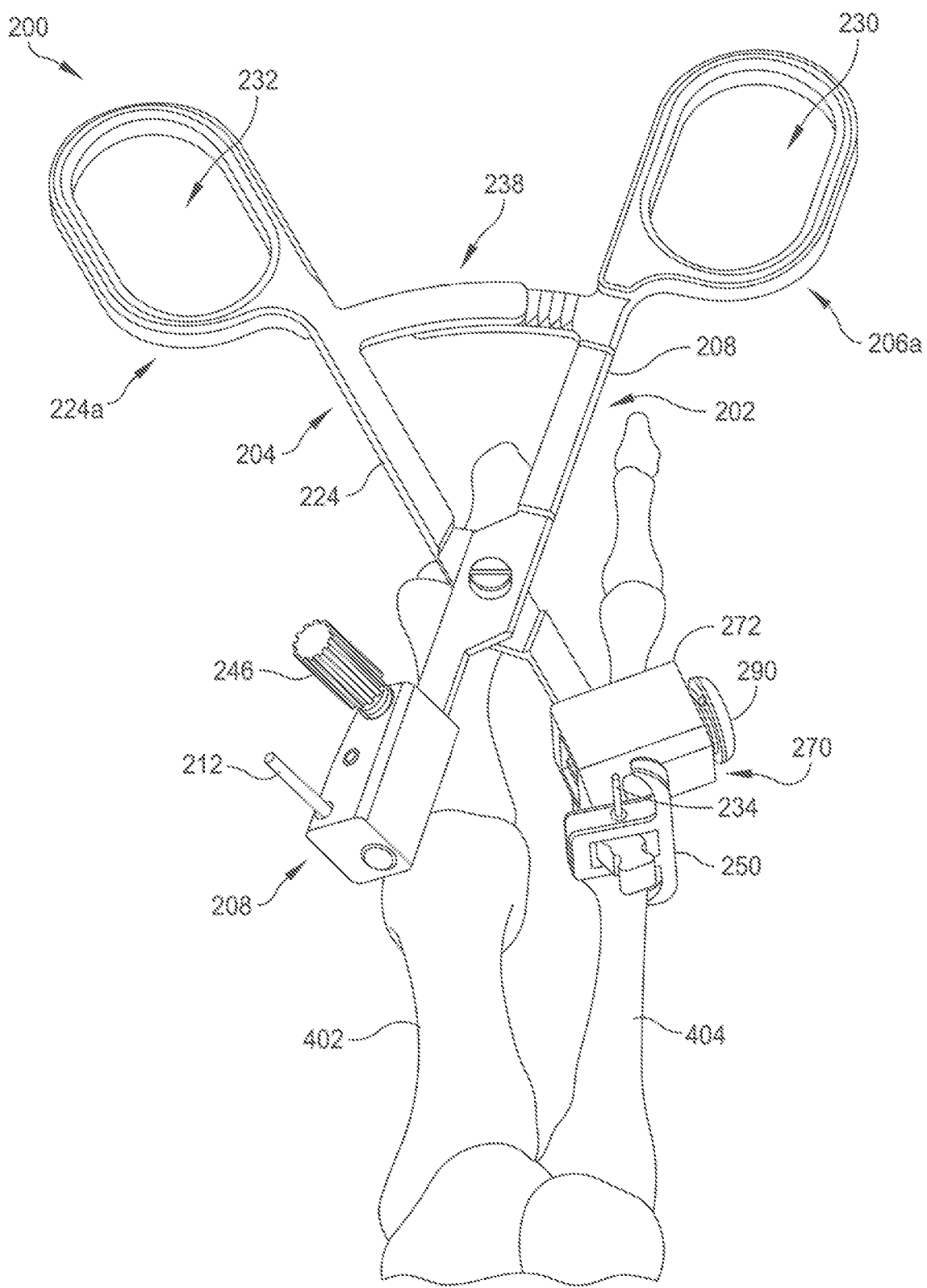
FIG. 21 is a perspective view of the device of FIG. 13 in use.

The release mechanism 274 is configured to allow a user to easily detach the coupler 270 from the second arm body 224 during use. The release mechanism 274 can be any mechanism that is appropriate for such a release. For example, as shown in FIGS. 14 and 15, the release mechanism 274 can include a slide 288, a button 290, and a biasing member 292. The slide 288 is configured to releasably engage the second arm body 224. For example, as shown in FIGS. 18 and 19, the slide 288 can include a stem 294 configured to be disposed in the passage 278 of the coupler body 272. A channel 296 is defined through the stem 294 and is configured to receive a portion of the second arm body 224. The coupler body 272 further includes a tab 298 projecting into the channel 296. The tab 298 is configured to engage a notch 300 in the second arm body 224 (shown in FIG. 20) to couple the coupler 270 to the second arm body 224.

The slide 288 can further include teeth 301 extending away from the center of the stem 294. As shown in FIG. 15, the teeth 301 are configured to engage a ledge 302 of the coupler body 272 to prevent the biasing force imparted by the biasing member 292 from pushing the slide 288 out of the passage 278. As shown in FIGS. 18 and 19, the teeth 301 can extend from flex arms 304 such that the flex arms 304 can flex inward, toward the center of the stem 294, during insertion of the stem 294 into the passage 278.

The button 290 can present an enlarged interface surface for engagement by a user. In some embodiments, the button 290 is integrally formed with the slide 288. In other embodiments, the button 290 is a separate component that is joined to the slide 288 using adhesives, fasteners, or any other appropriate fastening means.

As shown in FIG. 15, the biasing member 292 can be positioned in a cavity 306 in the coupler body 272 such that it biases the slide 288 and button 290 into a first position in which the slide 288 is engaged with the second arm body 224 (e.g., the tab 298 is engaged with the notch 300) and prevents removal of the coupler 270 from the second arm body 224. Depression of the button 290 moves the slide 288 to a second position in which the slide 288 disengages the second arm body 224 (e.g., the tab 298 disengages from the notch 300) such that the second arm body 224 can be removed from the coupler 270. The biasing member 292 can be any appropriate component that can impart a biasing force on the slide 288 and/or the button 290. For example, the biasing member 292 can be a helical compression spring, a compressible member (e.g., an elastomeric member), or any other appropriate component.

FIGS. 21-24 show the steps of use of the device 200 with the coupler 270. A pin 212 is inserted into the first bone 402. For example, the pin 212 can be inserted into the head of the first metatarsal. The pin 212 is preferably inserted at an oblique angle to the superior-inferior axis that is equal to or greater than the desired rotational correction of the first bone 402. The guide 208 is then slid over the pin 212 to engage the guide 208 with the first bone 402.

In addition, an incision is made in the space between the second and third metatarsals. The engagement member 250 is inserted into the incision such that it is positioned on the lateral side of the second bone 404 (e.g., the second metatarsal). The engagement member 250 can be attached to the projection 280 of the coupler 270 before the engagement member 250 is inserted into the incision. Alternatively, the engagement member 250 can first be inserted into the incision and then the coupler 270 can be attached to the coupler 270. For example, after insertion of the engagement member 250 into the incision, the projection 280 of the coupler body 272 can be inserted into the aperture 254 of the engagement member 250 and a pin 234 can be inserted through the aperture 282 in the projection 280 to attach the engagement member 250 to the coupler 270. In some embodiments, after inserting the projection 280 into the aperture 254, the user squeezes the first ends 206a, 224a of the first 206 and second 224 arm bodies together to ensure that the engagement member is in contact with the second bone 404. After the contact is secure, the pin 234 can be inserted into the second bone 404 to ensure that the engagement member 250 maintains engagement with the second bone 404 throughout the remainder of the procedure.

With the guide 208 coupled to the first bone via the pin 212 and the second arm 204 engaged with the second bone 404 via the engagement member 250 and/or the pin 234, the user can squeeze the first ends 206a, 224a of the first 206 and second 224 arm bodies to bring the first ends 206a, 224a together. This action reduces the angle between the first bone 402 and the second bone 404 and can also cause rotation of the first bone 402 in the frontal plane (i.e., around a longitudinal axis of the first bone 402). In addition, the user can manually rotate the first bone 402 toward the desired rotational position. When the first bone 402 reaches the desired rotational position, the user can tighten the locking screw 246 to lock rotation of the guide 208 with respect to the first arm body 206 and, thereby, secure the first bone 402 in the desired rotational orientation. In some embodiments, the user can continue to squeeze the first ends 206a, 224a of the first 206 and second 224 arm bodies to further reduce the angle between the first 402 and second 402 bones (e.g., the intermetatarsal angle) until the bones 402, 404 are in the desired position.

Figure 22:
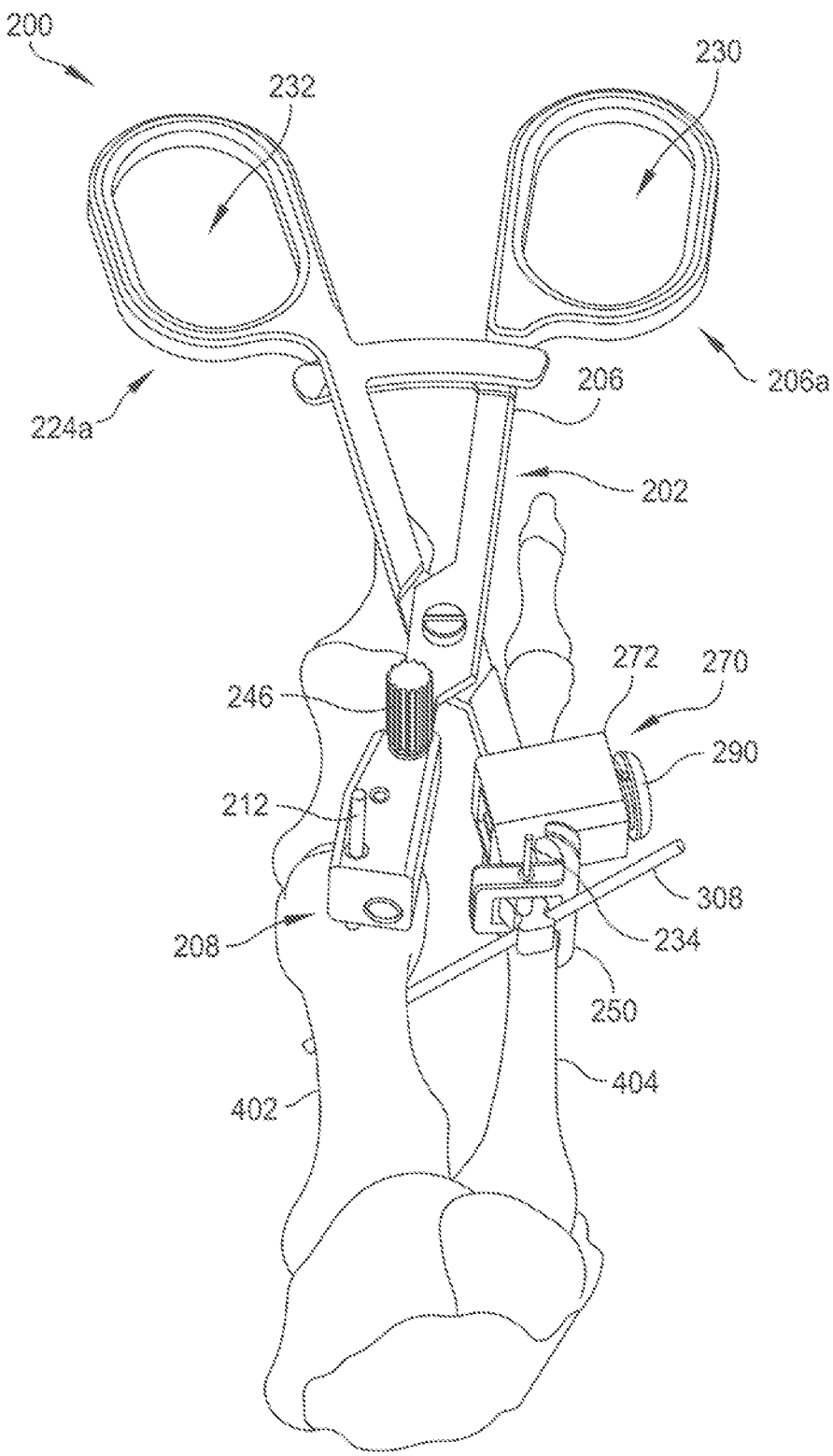
FIG. 22 is a perspective view of the device of FIG. 13 in use and after realignment of the bones.
Figure 23:
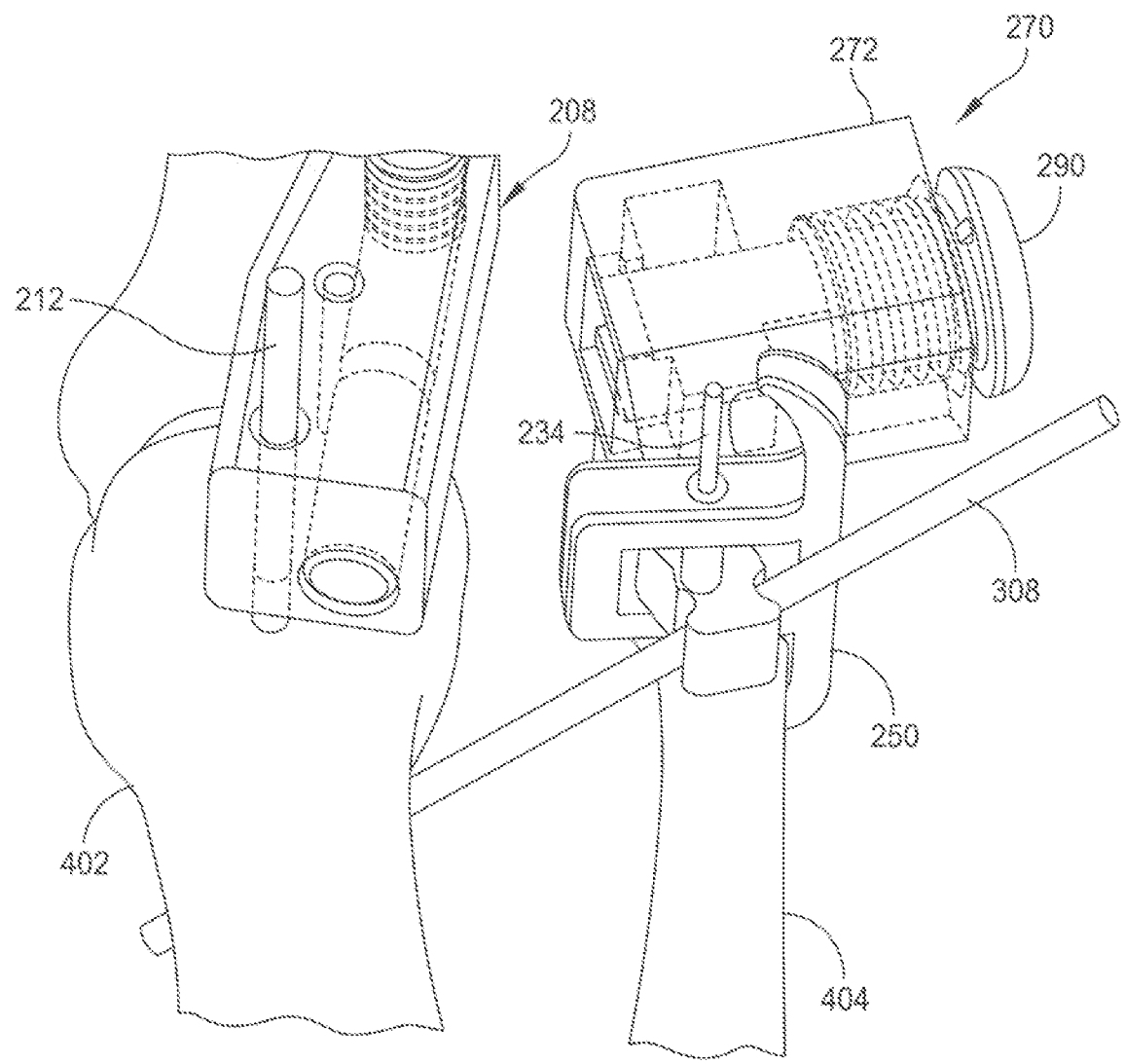
FIG. 23 is a detail view of a cross pin inserted into the first metatarsal using the device of FIG. 13.

With the bones 402, 404 in the desired position, the user can insert a pin 308 through the cross aperture 284 in the projection 280 of the coupler body 272 and into the first bone 402, as shown in FIG. 22. The pin 308 secures the first bone 402 in position and allows for the removal of the pin 212, as described below.

Figure 24:
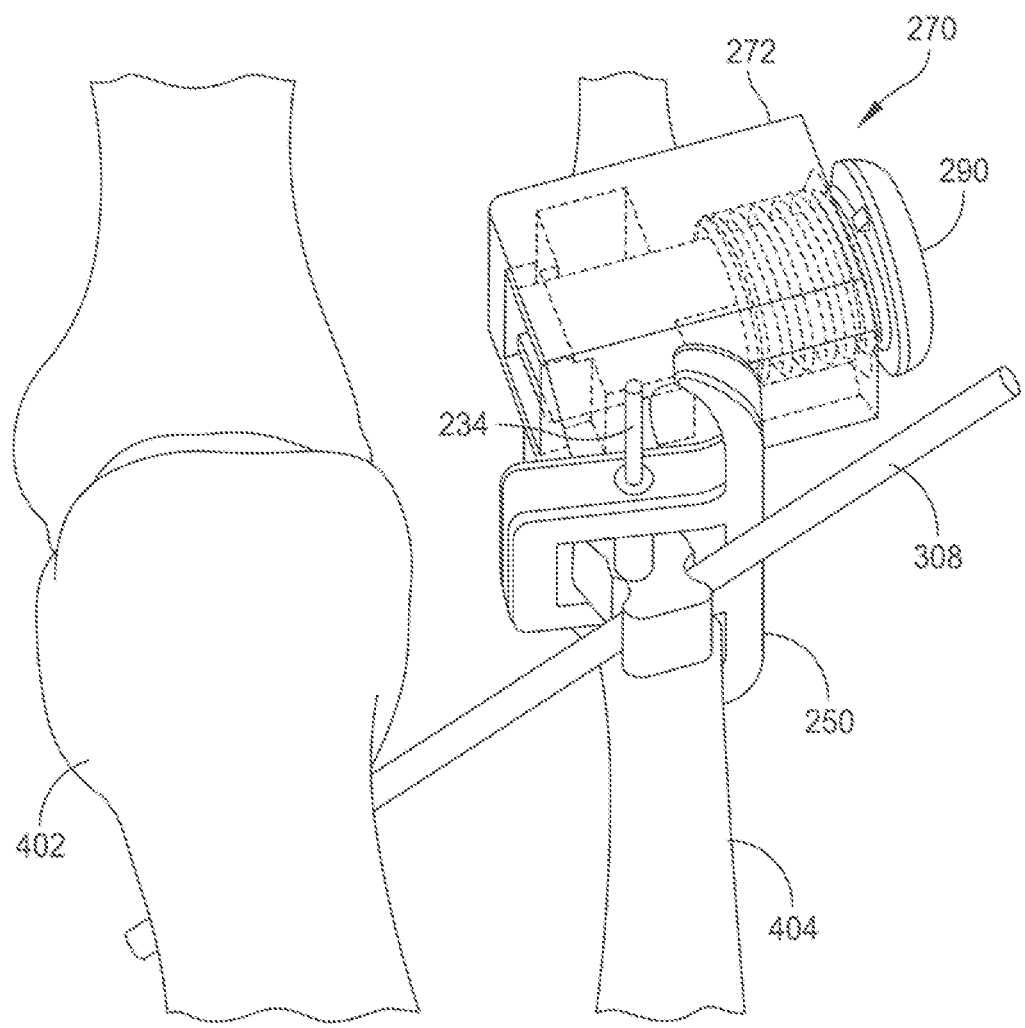
FIG. 24 is a view of the device of FIG. 13 in use and after removal of the guide and the first and second arm bodies.

With the pin 308 in place, the pin 212 can be removed. In addition, the release mechanism 274 can be actuated to disengage the second arm body 224 from the coupler 270. As a result, the second arm body 224 can be removed from the coupler 270, leaving the engagement member 250 and the coupler 270 engaged with the second bone 404 and the first bone 402 secured in position via the pin 308, as shown in FIG. 24.

A screw, plate, or other fixation device can then be used to secure the first bone 402 in place before removal of the pins 234, 308 and the coupler 270 and engagement member 250.

Figure 25:
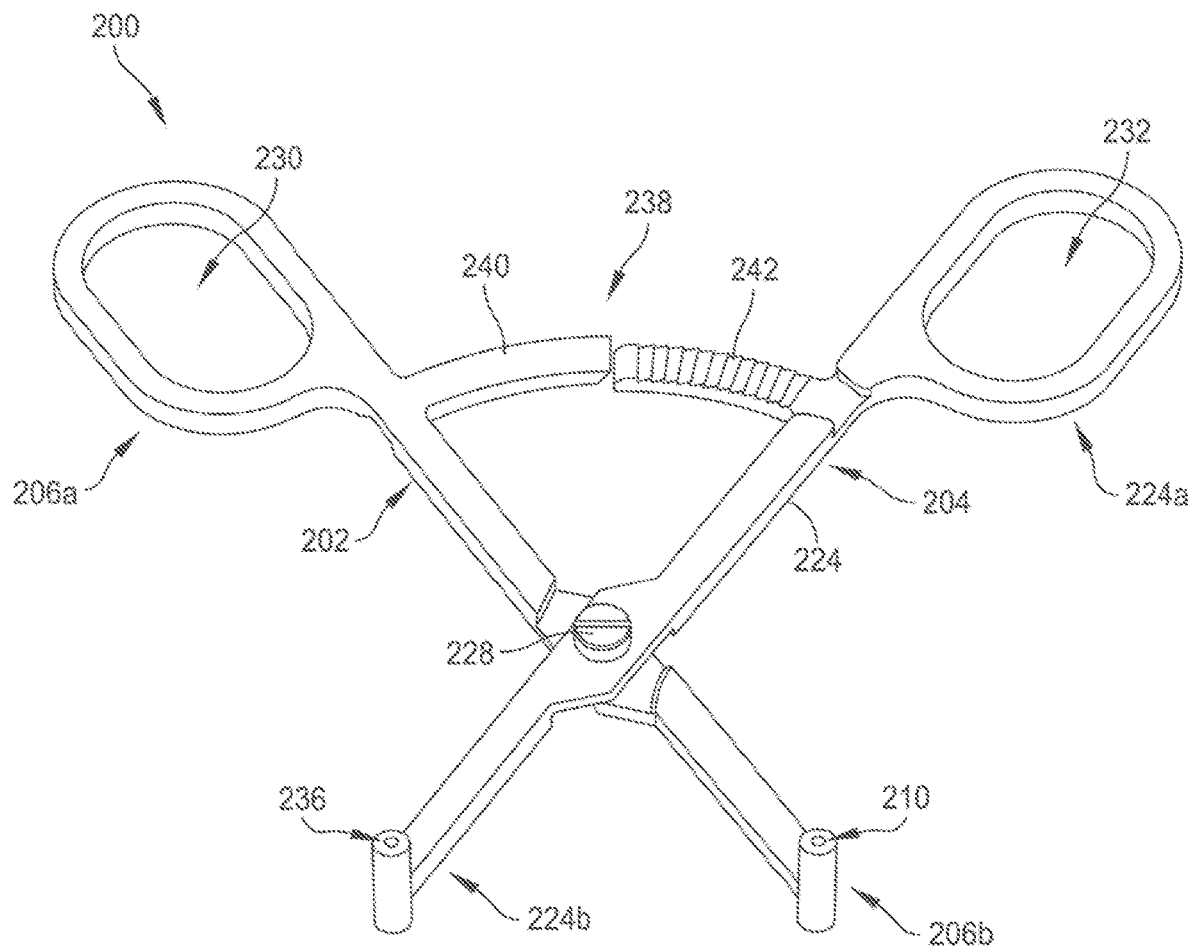
FIG. 25 shows a perspective view of a clamping device according to another embodiment described herein.

In other embodiments, shown in FIG. 25, the clamping device 200 does not include a rotatable guide. In using such an embodiment, the surgeon first inserts the first pin 212 at an angle that allows for the desired rotational correction (e.g., using fluoroscopy or another imaging modality). The surgeon then rotates the first bone 402 in the frontal plane (e.g., about a longitudinal axis of the bone) until the pin 212 aligns with the aperture 210 in the guide 208. The surgeon then couples the clamping device 200 to the first pin 212 and the second pin 234 and reduces the hallux valgus angle by bringing the first arm body 206 nearer the second arm body 224.

Figure 26A:
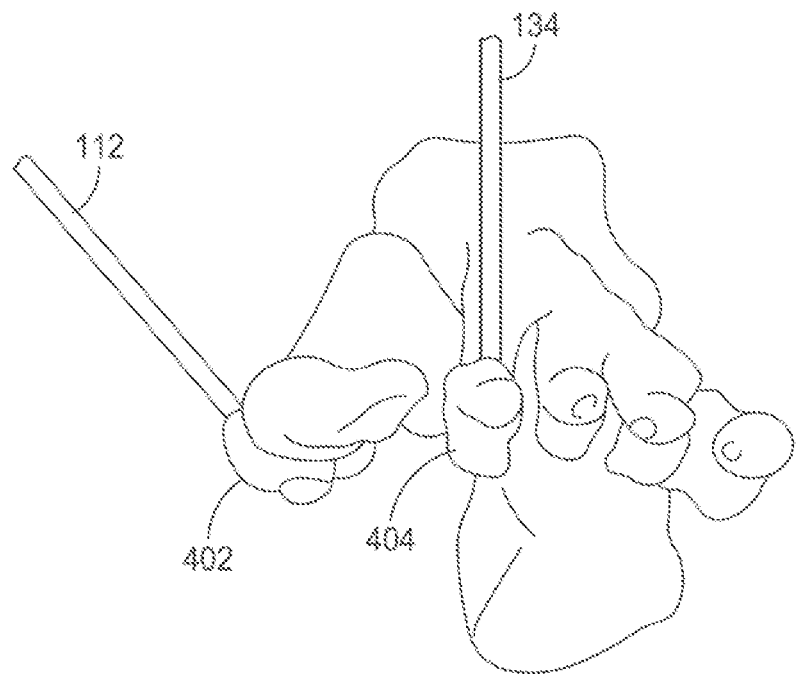
FIG. 26A shows a front view of a foot prior to reduction of the hallux valgus angle and correction of the rotational orientation of the first metatarsal.
Figure 26B:
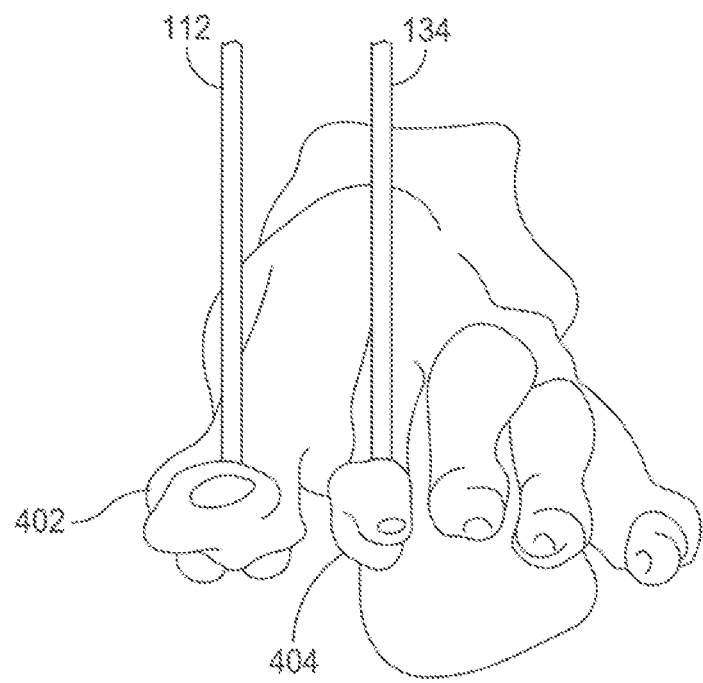
FIG. 26B shows a front view of a foot after reduction of the hallux valgus angle and correction of the rotational orientation of the first metatarsal.
Figure 27:
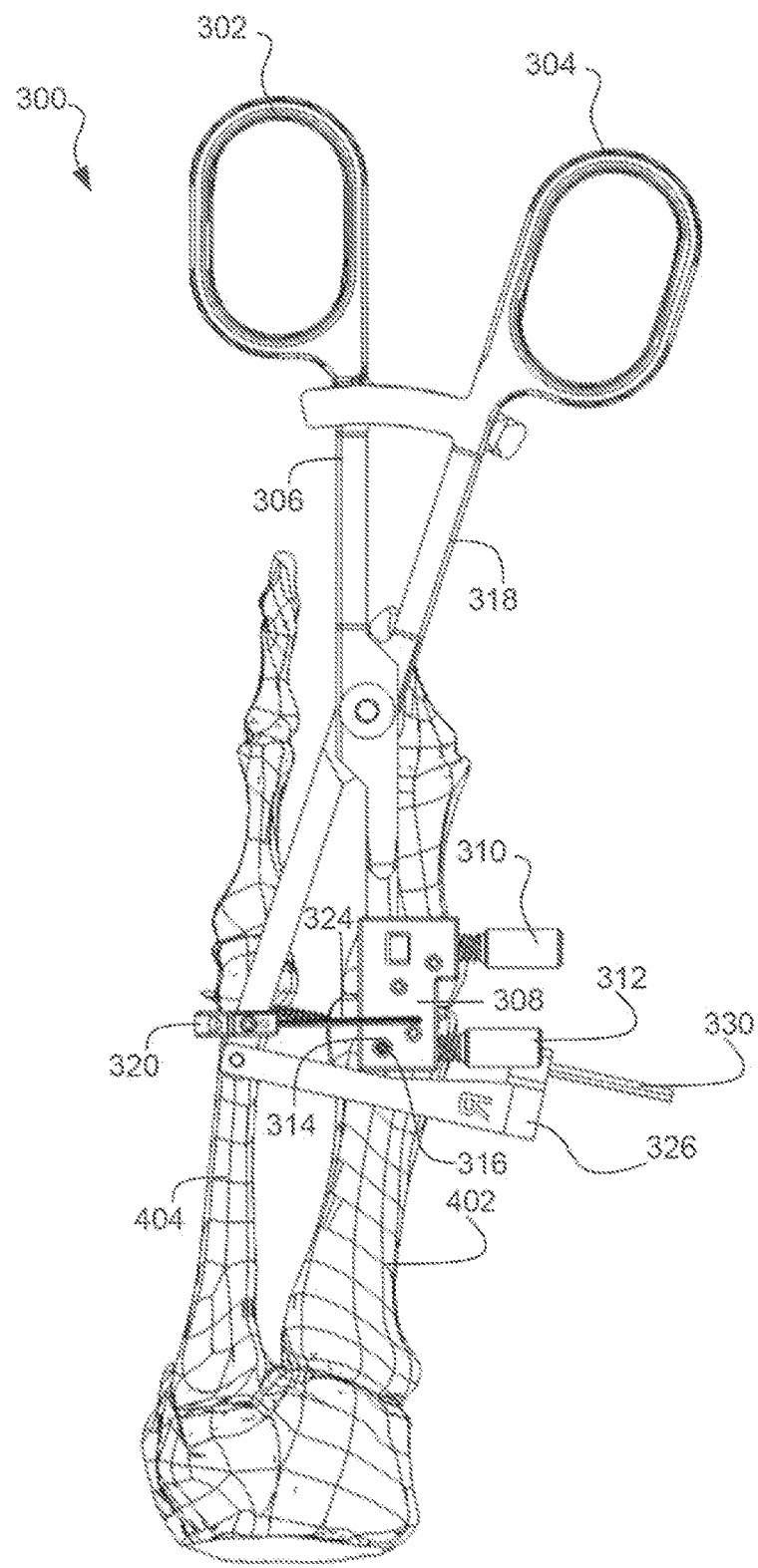
FIG. 27 is a top view of a clamping device according to another embodiment described herein.
Figure 28:
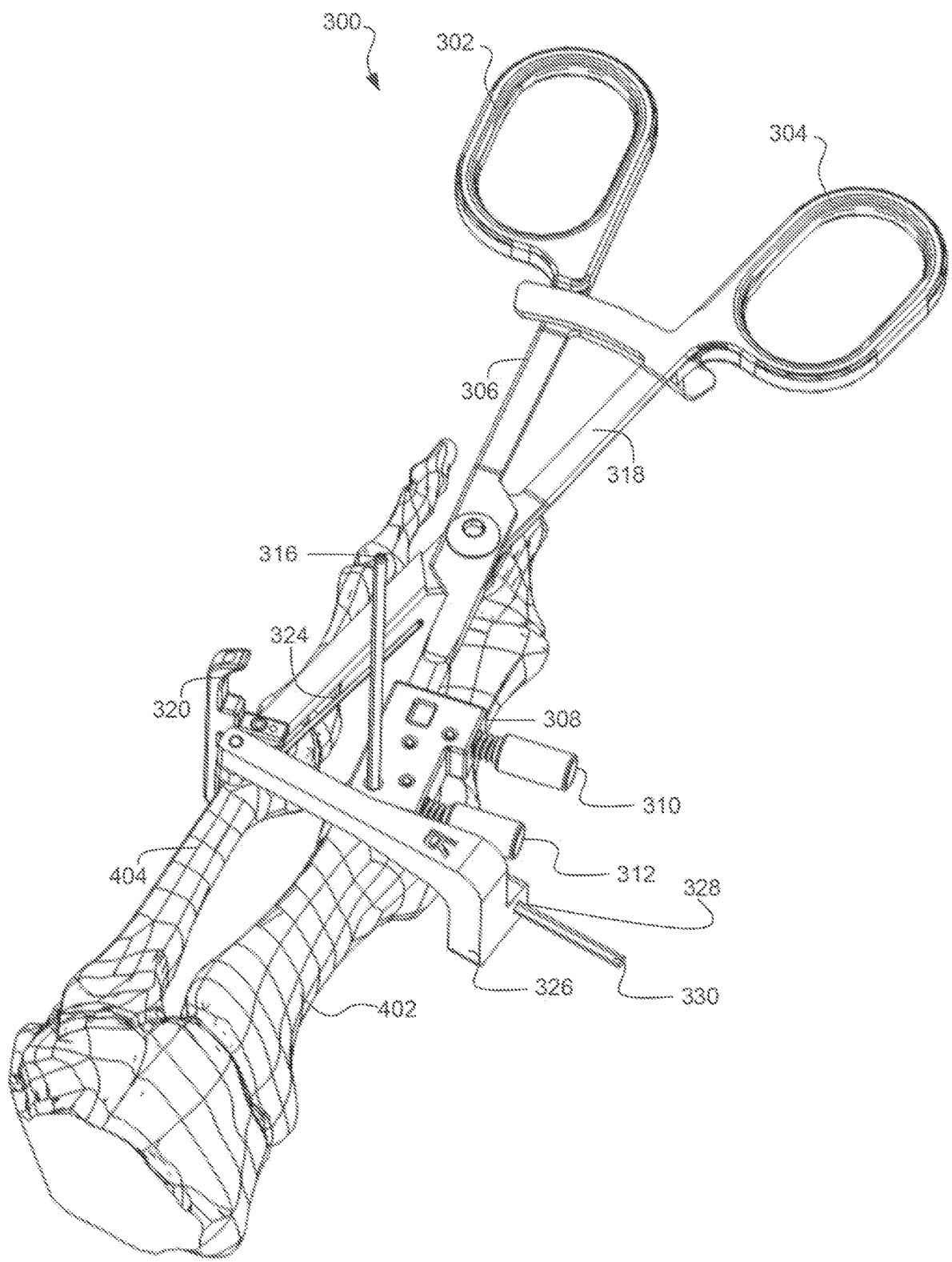
FIG. 28 is a perspective view of the clamping device of FIG. 27.
Figure 29:
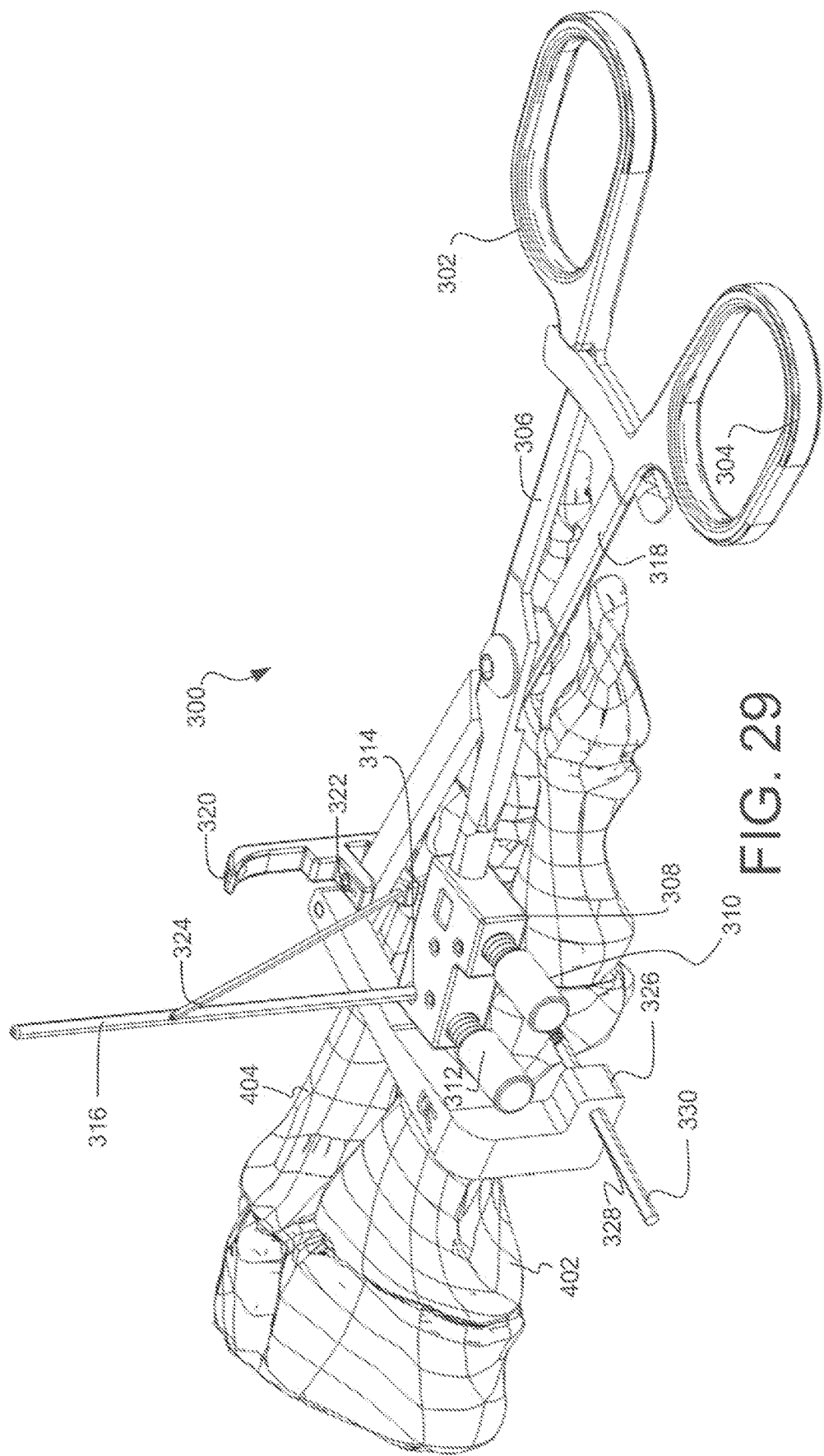
FIG. 29 is another perspective view of the clamping device of FIG. 27.
Figure 30:
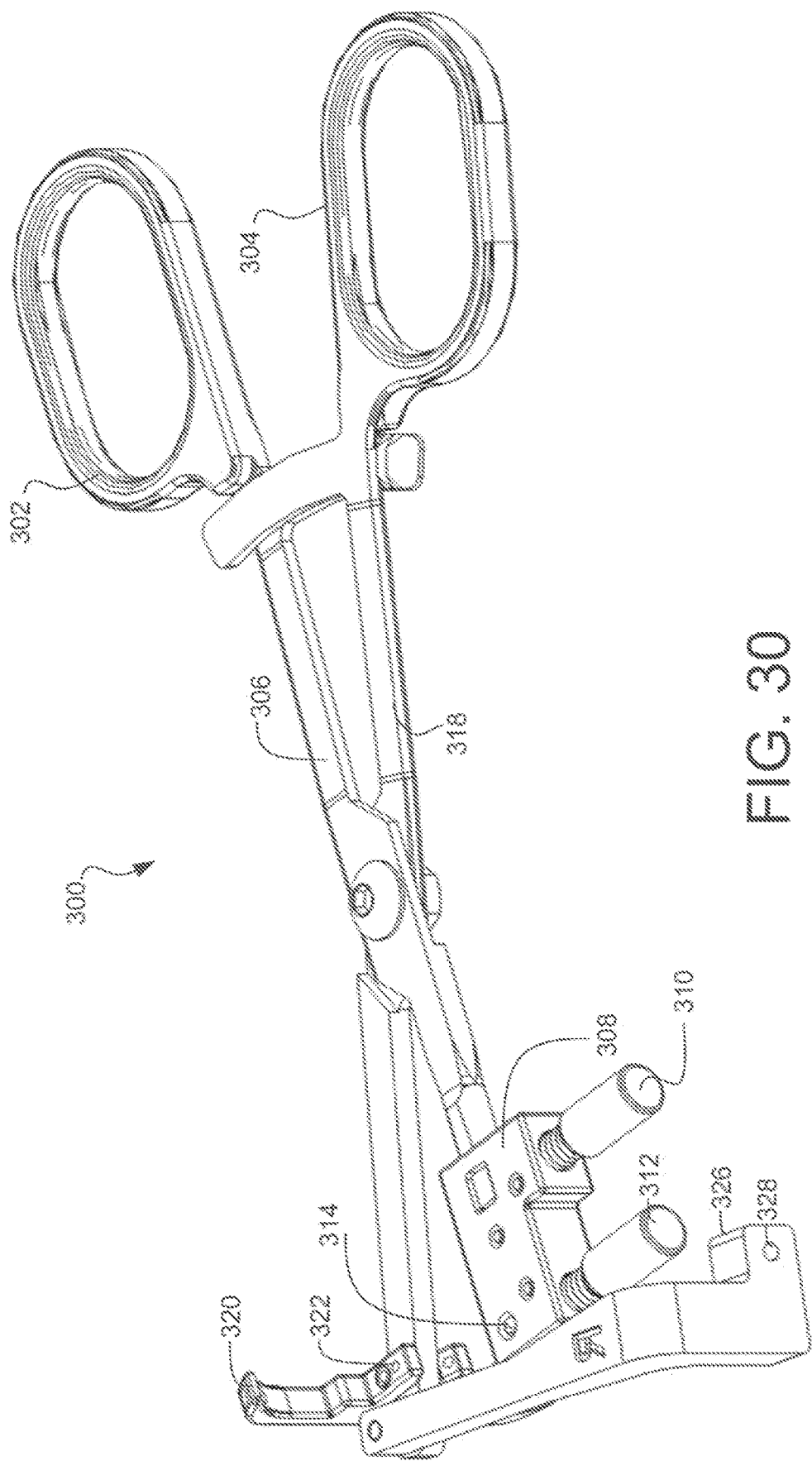
FIG. 30 is a perspective view of the clamping device of FIG. 27 without showing the bones to which the device may be attached.

FIGS. 26A and 26B show the realignment of the first metatarsal 402 using any of the clamping devices described herein. Only the pins 112, 134 are shown for ease of illustration. As shown in FIG. 26A, initially the first metatarsal 402 is deviated medially and is rotated in the frontal plane such that the sesamoids are positioned laterally with respect to the metatarsal head. The pin 112 is oriented such that it extends at an angle relative to the superior-inferior axis of the patient. As shown in FIG. 26B, after the procedure, the first metatarsal 402 is rotated in the frontal plane such that the sesamoids are positioned under the metatarsal head and the first metatarsal 402 is in the desired position. For example, in some embodiments, the first metatarsal 402 is rotated until the pin 112 is substantially parallel to the superior-inferior axis of the patient and to the pin 134. The distance between the first metatarsal head and the second metatarsal in the medial-lateral direction is also reduced such that the hallux valgus angle is reduced.

In another aspect, a method of reducing a hallux valgus angle and correcting a rotational alignment of a first metatarsal includes inserting a pin into the first metatarsal and through an aperture of a guide of a clamping device having a first arm rotatably coupled to a second arm, the guide being rotatably coupled to the first arm. The method further includes engaging the second arm with a second metatarsal. In some embodiments, engaging the second arm with the second metatarsal includes inserting a pin into the second metatarsal and through an aperture of the second arm. In other embodiments, engaging the second arm with the second metatarsal includes contacting a lateral side of the second metatarsal with a hook of the second arm. The method further includes rotating the first arm with respect to the second arm to reduce the distance between the first metatarsal and the second metatarsal and, thereby, the hallux valgus angle. The method further includes locking rotation of the guide with respect to the first arm. In some embodiments, locking rotation of the guide includes rotating a locking screw or a locking nut. In some embodiments, the method further includes, after locking rotation of the guide, further rotating the first arm with respect to the second arm to further reduce the distance between the first metatarsal and the second metatarsal.

In some embodiments, the method further includes inserting a cross pin through a coupler attached to the second arm and into the first bone such that the pin is at an oblique angle to the sagittal plane. The method can further include removing the first pin inserted in the first bone and detaching the second arm body from the coupler.

In another aspect, a method of reducing a hallux valgus angle and correcting a rotational alignment of a first metatarsal includes inserting a pin into the first metatarsal. The method further includes rotating the first metatarsal in the frontal plane (e.g., around a longitudinal axis of the first metatarsal) using the pin. The method further includes coupling a clamping device to the pin by sliding an aperture of a first arm of the clamping device over the pin. The method further includes engaging a second arm of the clamping device with a second metatarsal. The method further includes rotating the first arm with respect to the second arm to reduce the distance between the first metatarsal and the second metatarsal.

The methods described above may further include various steps to prepare the foot for the procedure, including, for example, debriding the tarsometatarsal joint.

FIGS. 27-30 illustrate another embodiment of a clamping device 300. The clamping device 300 may include similar features to those described in relation to devices 100 and 200 and may include components that function in the same or a similar manner. In an exemplary embodiment, the device 300 includes a first arm 302, a second arm 304, and a threaded pin guide 326. The first arm 302 includes a first arm body 306, a guide 308, a first locking screw 310, and a second locking screw 312. The guide 308 is coupled to a distal end of the first arm body 306. The guide 308 defines an aperture 314 adapted to receive a pin 316 inserted in a first bone 402, such as a first metatarsal. The guide 308 is rotatable with respect to the first arm body 306 about a guide axis defined by the first arm body 306.

The second arm 304 includes a second arm body 318 and an engagement member 320. The engagement member 320 includes a second aperture 322 adapted to receive a pin 324 inserted in a second bone 404. In use, rotation of the second arm body 318 with respect to the first arm body 306 changes the distance between the first bone 402 and the second bone 404 and rotation of the guide 308 with respect to the first arm body 306 rotates the first bone 402 (e.g., in the frontal plane). The clamping device 300 can further include a locking mechanism configured to lock the position of the first arm body 306 relative to the second arm body 318, such as via locking teeth described in relation to the previous embodiments. The threaded pin guide 326 is configured to connect to the distal end of the second arm body 318 and bridge across the first bone 402 and second bone 404 to provide an aperture 328 for a threaded pin 330 to be inserted medially through the first bone 402 and the second bone 404.

Figure 31:
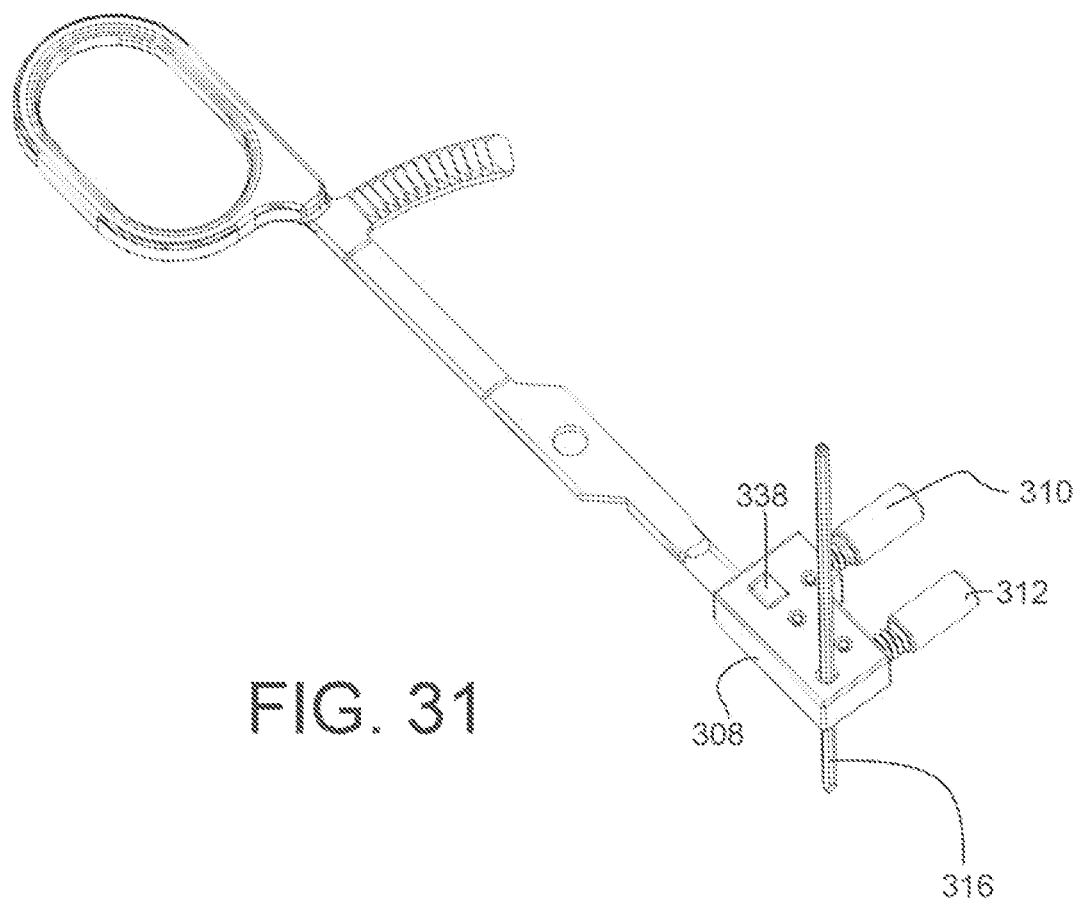
FIG. 31 is a perspective view of the first arm of the clamping device of FIG. 27.
Figure 32:
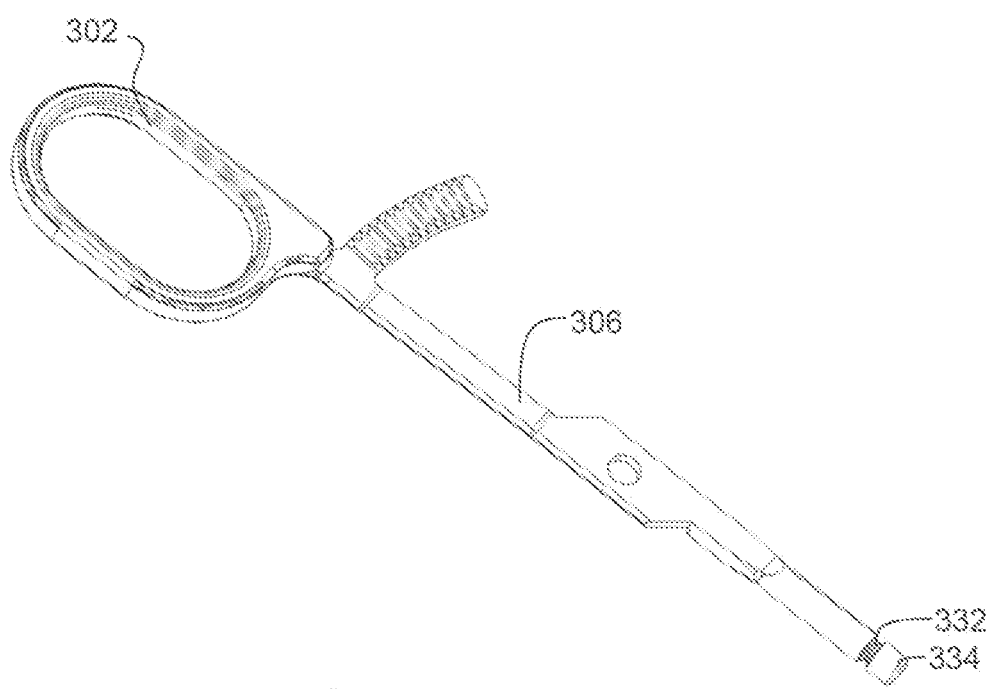
FIG. 32 is a perspective view of a first arm body of a first arm of the clamping device of FIG. 27.
Figure 34:
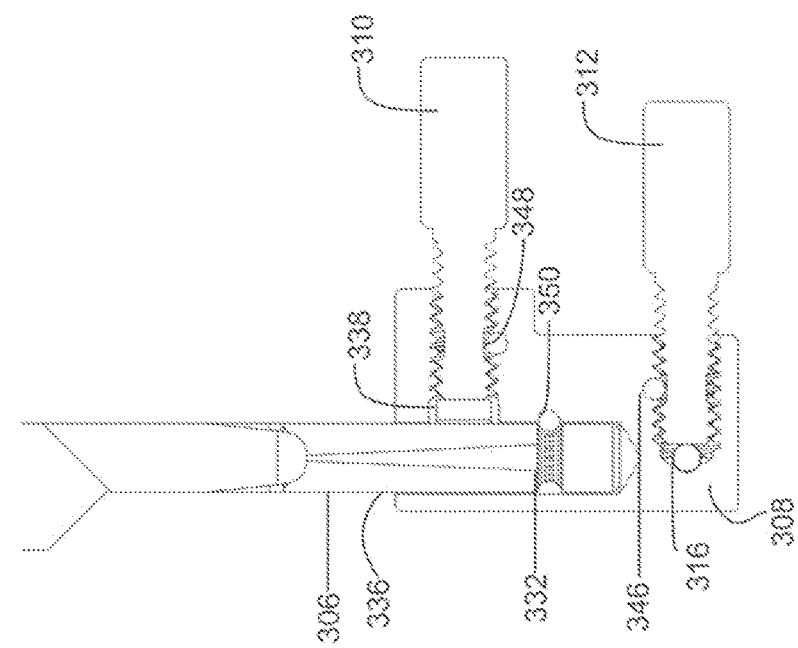
FIG. 34 is a cross-sectional view of the first arm of FIG. 33.

FIGS. 31-35 further illustrate the components of the first arm 304. FIG. 31 shows the completed assembly of the first arm 304, including the pin 316 inserted into the aperture 314. FIG. 32 includes a view of the first arm body 306. The first arm body 306 includes a distal end having a cylindrical structure and including a groove 332 and an end portion 334. The distal end is configured to be inserted into a hole 336 in the guide 308 (FIG. 34). The hole 336 may be a blind hole that extends through only a portion of the guide 308 (i.e., not a through-hole).

The first locking screw 310 is coupled to the guide 308. Rotation of the first locking screw 310 in a first direction (e.g., clockwise) locks rotation of the guide 308 with respect to the first arm body 306 and rotation of the first locking screw 310 in a second direction (e.g., counter-clockwise) releases rotation of the guide 308 with respect to the first arm body 306. In some embodiments, the guide 308 defines the hole 336 and a portion of the first arm body 306 extends through the hole 336 and the first locking screw 310 is configured to engage a portion of the first arm body 306 that extends through the guide 308 to restrict rotation of the guide 308. As shown best in FIG. 35, the first locking screw 310 may be connected to a rotation lock adapter 338 configured to engage the first arm body 306. The rotation lock adapter 338 may include a crescent shape and configured to translate in a medial-lateral direction to engage the first arm body 306 and lock rotation of the guide 308. The second locking screw 312 is coupled to the guide 308 and is configured to engage the pin 316 to inhibit movement of the pin 316 during use. The first locking screw 310 and the second locking screw 312 may be generally directed in a medial direction which may help to promote symmetry and use on either foot of a patient.

Figure 33:
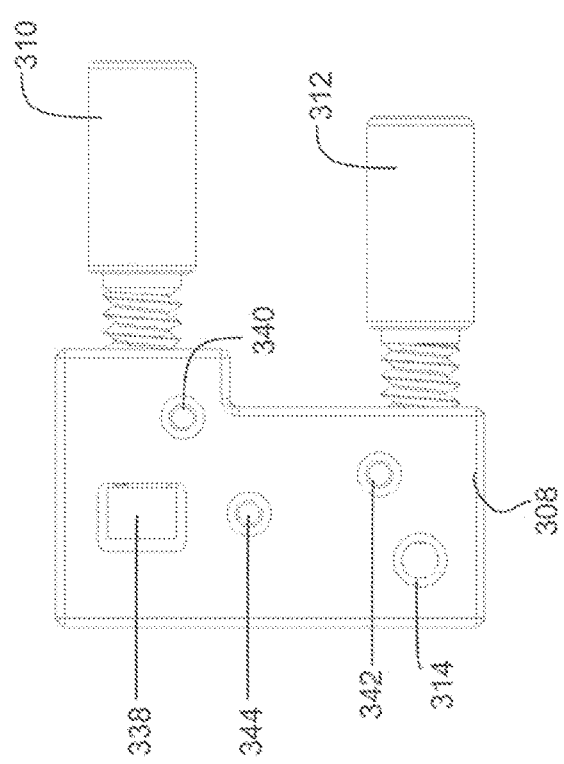
FIG. 33 is a top view of a guide of the first arm of the clamping device of FIG. 27.

As shown in FIGS. 33-34, the guide 308 may include pin openings 340, 342, and 344 configured to receive rotation guide pins 346, 348, and 350, respectively. The rotation guide pins 346 and 348 may be inserted to guide rotation of the threads of the locking screws 310, 312, respectively (thereby enabling them to translate forward and backward in the corresponding holes in the guide 308). The rotation guide pin 350 may be configured to be at least partially disposed in the groove 332. During assembly, the rotation guide pin 350 is inserted into the hole 344 and the groove 332 to axially position the guide 308 and prevent inadvertent removal of the guide 308 from the first arm body 306.

FIG. 36 includes an exploded view of the second arm 304, including the second arm body 318 and engagement member 320, and the threaded pin guide 326. The second arm body 318 is coupled to the first arm body 306 such that the second arm body 318 is rotatable with respect to the first arm body 306 about a rotation axis defined by a connecting screw or pin 352. In some embodiments, the transverse guide axis of the guide 308 and rotation axis of the screw or pin 352 are perpendicular to one another.

The second arm body 318 includes a first connecting aperture 354 configured to receive a pin 356 to connect the engagement member 320 to the second arm body 318 at the distal end of the second arm body 318. The second arm body 318 further includes a second connecting aperture 358 configured to receive a pin 360 to connect the threaded pin guide 326 to the distal end of the second arm body 318.

Figure 37B:
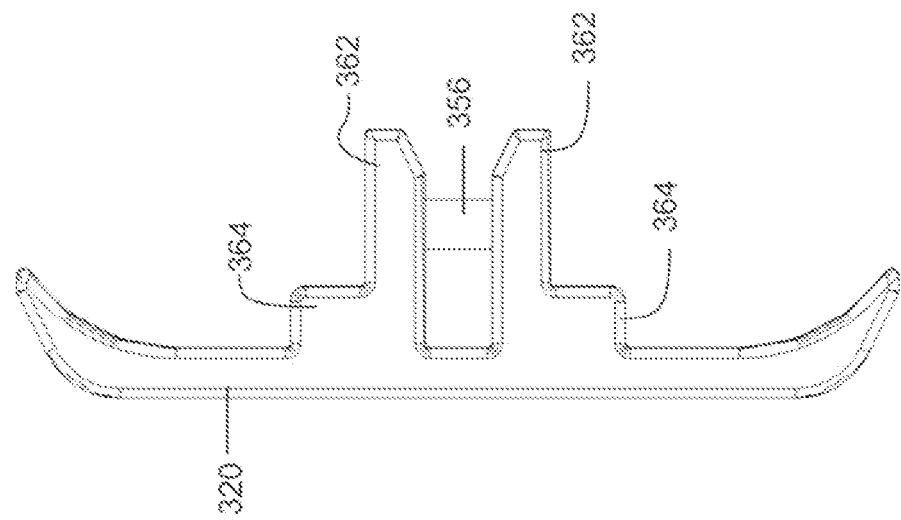
FIG. 37B is a side view of the engagement member of FIG. 37A.
Figure 37A:
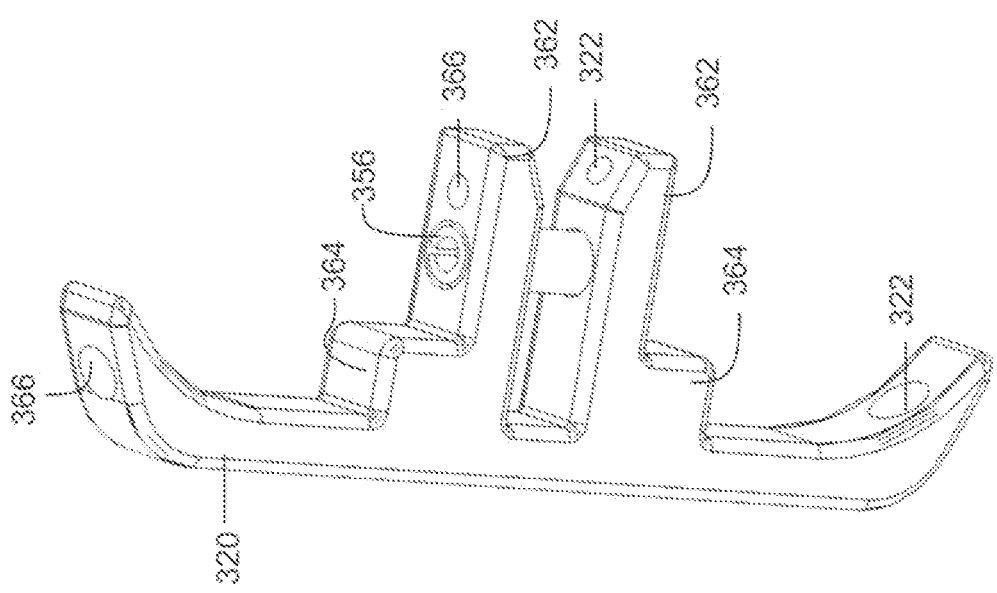
FIG. 37A is a perspective view of an engagement member of the clamping device of FIG. 27.

FIGS. 37A-37B further illustrate an embodiment of the engagement member 320. The engagement member 320 includes a pair of projections 362 configured to be placed on opposing sides of the second arm body 318 and receive the pin 356 therethrough to thereby connect the engagement member 320 to the second arm body 318. The engagement member 320 further includes an intermediate section including a pair of bumps 364 to better locate bone engagement in use. Engagement member 320 further includes the second aperture 322 for receiving the pin 324. In an embodiment, the second aperture 322 incudes a pair of aligned apertures 322 to enable the pin 324 to be angled through the second bone 404. In order to enable use of the engagement member 320 on either foot, the engagement member 320 may be symmetrical. The engagement member 320 may include a second pair of aligned apertures 366 that may be used to receive the pin 324, such as when the device 300 is used with the opposite foot of the patient.

In many aspects, the steps of using the clamping device 300 can be similar to the steps of using clamping devices 100 and 200, as described above. The pin 324 is inserted into the second bone 404 (e.g., a second metatarsal) and the second arm 304 is coupled to the second bone 404 by passing the pin 324 through the aligned openings of the second aperture 322 in the engagement member 320. A pin 316 is inserted through the first aperture 314 in the guide 308 and into the first bone 402 (e.g., a first metatarsal). It should be understood that the steps of inserting the pins and coupling the device 300 to the pins can be performed in any desired order. For example, the pin 316 could first be inserted into the first bone 402. The guide 308 could then be placed over the first pin 316 before the second pin 324 is inserted through the aperture 322 and into the second bone 404. In some embodiments, the threaded pin guide 336 may be connected and threaded pin 330 inserted through adjacent bones (e.g., metatarsal heads) for further securing the bones in position.

As described above, the first bone 402 is rotated in the frontal plane (i.e., about a longitudinal axis of the first bone 402). Rotation guide 308 rotates with respect to the first arm body 306 as the first bone 402 is rotated. With the first bone 402 in the desired rotational orientation, the surgeon can rotate the first locking screw 310 to lock rotation of the guide 308.

Further, the surgeon can also squeeze the proximal end of the first arm body 306 toward the proximal end of the second arm body 318. In so doing, the distal end of the first arm body 306 is brought nearer to the distal end of the second arm body 318, thereby reducing the hallux valgus angle. It should be understood that the rotation of the guide 308 can be locked before or after reducing the hallux valgus angle. For example, in some procedures, the surgeon may allow the guide 308 to be rotatable about the guide axis of the first arm body 306 while reducing the hallux valgus angle such that the first bone 402 (e.g., the first metatarsal) is able to rotate in the frontal plane (e.g., about a longitudinal axis of the bone) while the hallux valgus angle is reduced. This may allow for the natural anatomy of the bones of the foot, for example the contacting surfaces of the first metatarsal and tarsal bones, to cause rotation of the bone in the frontal plane toward a more natural position. In some embodiments, rotation of the guide 308 is unlocked during a first portion of the reduction of the hallux valgus angle and rotation of the guide 308 is then locked before completing reduction of the hallux valgus angle.

With the hallux valgus reduced as desired, a locking mechanism (e.g., locking teeth) can maintain the relative positions of the first arm body 306 and the second arm body 318 to maintain the position of the first bone 402 and the second bone 404. A plate, screw, suture, or other means of fixation can then be applied to the bones to hold them in position before removing the pins 316, 324, 330 and clamping device 300.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A device, comprising:
   a first arm comprising:
      a first arm body extending along a longitudinal axis from a first end to a second end; and
      a guide coupled to the second end of the first arm body, wherein the guide is configured to be coupled to a first bone, and wherein the guide is rotatable with respect to the first arm body about the longitudinal axis, wherein the guide includes a first plate and a second plate, and wherein the first and second plates together define an aperture adapted to receive a pin inserted in the first bone to couple the guide to the first bone;
   a second arm including a second arm body extending from a first end to a second end, the second arm body directly coupled to the first arm body such that the second arm body is rotatable with respect to the first arm body about a rotation axis, wherein the second arm is configured to engage a second bone at the second end of the second arm body; and
   wherein, in use, rotation of the second arm body with respect to the first arm body is configured to change a distance between the first bone and the second bone and rotation of the guide with respect to the first arm body is configured to rotate the first bone about a longitudinal axis of the first bone.

2. The device of claim 1, wherein the first and second plates each define a bore transverse to the aperture, and wherein the first arm body passes through the bore of each of the first and second plates.

3. The device of claim 2, wherein the first arm body includes a threaded end and the device further comprises a nut engaged with the threaded end such that rotation of the nut in a first direction clamps the plates and locks rotation of the guide and rotation of the nut in a second direction releases rotation of the guide.

4. The device of claim 1, wherein the guide rotates with respect to the first arm body about an axis that is transverse to the rotation axis.

5. The device of claim 1, wherein the rotation axis is intermediate the respective first and second ends of the first and second arm bodies.

6. The device of claim 1, wherein the second arm includes a second aperture at the second end of the second arm body, and wherein the second aperture is adapted to receive a pin inserted in the second bone.

7. The device of claim 1, wherein each of the first arm body and the second arm body includes a finger hole at its respective first end.

8. The device of claim 1, comprising a locking mechanism including a first locking arm extending from the first arm body and a second locking arm extending from the second arm body, the first and second locking arms each include teeth configured to engage with one another.

9. A system, comprising:
   a device, comprising:
      a first arm comprising:
         a first arm body extending along a longitudinal axis from a first end to a second end; and
         a guide coupled to the first arm body, wherein the guide is configured to be coupled to a first bone, and wherein the guide is rotatable with respect to the first arm body, wherein about the longitudinal axis the guide includes a first plate and a second plate, and wherein the first and second plates together define an aperture adapted to receive a pin inserted in the first bone to couple the guide to the first bone;
      a second arm including a second arm body extending from a first end to a second end, the second arm body directly coupled to the first arm body such that the second arm body is rotatable with respect to the first arm body about a rotation axis, wherein the second arm is configured to engage a second bone at the second end of the second arm body; and
   wherein, in use, rotation of the second arm body with respect to the first arm body is configured to change a distance between the first bone and the second bone and rotation of the guide is configured to rotate the first bone about a longitudinal axis of the first bone.

10. The system of claim 9, further comprising the pin configured to be inserted in the first bone.

11. The system of claim 10, wherein the pin is a k-wire.

12. The system of claim 9, wherein the first and second plates each define a bore transverse to the aperture, and wherein the first arm body passes through the bore of each of the first and second plates.

13. The system of claim 12, wherein the first arm body includes a threaded end and the device further comprises a nut engaged with the threaded end such that rotation of the nut in a first direction clamps the plates and locks rotation of the guide and rotation of the nut in a second direction releases rotation of the guide.

14. The system of claim 9, wherein the guide rotates about an axis that is transverse to the rotation axis.

15. The system of claim 9, wherein the rotation axis is intermediate the respective first and second ends of the first and second arm bodies.

16. The system of claim 9, wherein the second arm includes a second aperture at the second end of the second arm body, and wherein the second aperture is adapted to receive a second pin inserted in the second bone such that the engagement of the second arm with the second bone is via the second pin.

17. The system of claim 9, wherein each of the first arm body and the second arm body includes a finger hole at its respective first end.

* * * * *